(12) United States Patent
Zakharov et al.

(10) Patent No.: US 12,201,455 B2
(45) Date of Patent: Jan. 21, 2025

(54) TECHNIQUE FOR DETERMINING A RISK INDICATOR FOR MYOPIA

(71) Applicant: Vivior AG, Zurich (CH)

(72) Inventors: Pavel Zakharov, Volketswil (CH);
Daniel Ian Flitcroft, Dublin (IE);
Michael Mrochen, Zug (CH)

(73) Assignee: Carl Zeiss Vision GmbH, Aalen (DE)

( * ) Notice: Subject to any disclaimer, the term of this patent is extended or adjusted under 35 U.S.C. 154(b) by 506 days.

(21) Appl. No.: 17/624,391

(22) PCT Filed: Jun. 9, 2020

(86) PCT No.: PCT/EP2020/065946
§ 371 (c)(1),
(2) Date: Jan. 3, 2022

(87) PCT Pub. No.: WO2021/001120
PCT Pub. Date: Jan. 7, 2021

(65) Prior Publication Data
US 2022/0354436 A1    Nov. 10, 2022

(30) Foreign Application Priority Data

Jul. 4, 2019    (EP) .................................... 19184427

(51) Int. Cl.
*A61B 5/00*    (2006.01)
*A61B 3/00*    (2006.01)
(Continued)

(52) U.S. Cl.
CPC .......... *A61B 5/7275* (2013.01); *A61B 3/0091* (2013.01); *A61B 3/113* (2013.01);
(Continued)

(58) Field of Classification Search
CPC ..... A61B 5/7275; A61B 3/0091; A61B 3/113; A61B 3/14; A61B 5/065; A61B 5/1114;
(Continued)

(56) References Cited

U.S. PATENT DOCUMENTS 9,195,074 B2    11/2015    Bakaraju et al.
2015/0277145 A1*    10/2015    Bakaraju ................ G02C 7/041
351/159.01

FOREIGN PATENT DOCUMENTS

WO    2014174067    10/2014

OTHER PUBLICATIONS

Search Report for European Patent Application No. 19184427.3, European Patent Office, Feb. 6, 2020.
(Continued)

*Primary Examiner* — James C. Jones
(74) *Attorney, Agent, or Firm* — Williams Mullen; Thomas F. Bergert

(57) ABSTRACT

A system is provided for determining a risk indicator for myopia. The system comprises a wearable device configured to be attached to a body of a user. The wearable device comprises at least one distance sensor configured to determine at least a first distance value indicative of a distance between the wearable device and an object located in a central vision zone of the user and a second distance value indicative of a distance between the wearable device and an object located in a peripheral vision zone of the user. The system further comprises a control unit configured to determine, based on the first distance value and the second distance value, a risk indicator for myopia. Further, a method and a computer program product are provided.

15 Claims, 11 Drawing Sheets

(51) Int. Cl.
*A61B 3/113* (2006.01)
*A61B 3/14* (2006.01)
*A61B 5/06* (2006.01)
*A61B 5/11* (2006.01)

(52) U.S. Cl.
CPC ............... *A61B 3/14* (2013.01); *A61B 5/065* (2013.01); *A61B 5/1114* (2013.01); *A61B 5/6803* (2013.01); *A61B 2562/0219* (2013.01)

(58) Field of Classification Search
CPC .......... A61B 5/6803; A61B 2562/0219; A61B 3/103; A61B 3/112; A61B 3/1173; G16H 40/63; G16H 40/67; G16H 50/20; G16H 50/30; G16H 50/50; G02C 11/10; G02C 2202/24
See application file for complete search history.

(56) References Cited

OTHER PUBLICATIONS

International Search Report and Written Opinion for PCT/EP2020/065946, European Patent Office, Sep. 11, 2020.
Flitcroft, D.I. : "The complex interactions of retinal, optical and environmental factors in myopia aetiology", Progress in Retinal and Eye Research, 31(6), 622-660, (2012).

* cited by examiner

TECHNIQUE FOR DETERMINING A RISK INDICATOR FOR MYOPIA

CROSS-REFERENCE TO RELATED APPLICATIONS

This application is the U.S. national phase of international application PCT/EP2020/065946, filed on Jun. 9, 2020, which claims the benefit of Eurpoean application EP 19184427.3 filed on Jul. 4, 2019; all of which are hereby incorporated herein in their entirety by reference.

TECHNICAL FIELD

The present disclosure relates to the field of ophthalmology. More precisely, the present disclosure is directed to a technique for determining a risk indicator for myopia. In particular, the risk indicator may indicate a risk of myopia onset and/or progression. The technique may be embodied in at least one system and/or at least one method.

BACKGROUND

It is known that myopia (nearsightedness), in particular of children, may be caused by eye growth. In this case, eye growth causes the eye to be too large so that the image is formed not on the retina (as it should be) but in front of the retina, i.e., within the eye.

It is further known that a phenomenon called "hyperopic defocus", wherein the image is formed behind the retina of the eye, may cause the eye growth which might lead to myopia. Further details regarding myopia in general and regarding the aforementioned phenomenon are described, e.g., in Flitcroft, D. I. (2012): "The complex interactions of retinal, optical and environmental factors in myopia aetiology", Progress in Retinal and Eye Research, 31(6), 622-660.

The accommodation error or accommodation lag is a mismatch of the focusing state of the eye (accommodation response) and the distance to the object being viewed (accommodation demand). Typically the eye under-accommodates for near-objects and the closer the distance the greater the degree of under-accommodation or "accommodation lag". This lag is a source of hyperopic defocus in the posterior part of the eye (the macula). Hyperopic defocus can also result from the shape of the posterior part of the eye, as myopic eyes often display relative peripheral hyperopia so that when corrected for distance the vision and viewing a distance object, the peripheral retina is exposed to hyperopic defocus. It can also result from the structure of the visual environment, where objects in the peripheral field are at a different distance to the object being viewed centrally because the accommodation system of the eye only adjusts to the focus demands in the central visual field.

Details describing these phenomena and the eye growth caused by these phenomena will be described further below.

At the moment, several techniques are known to correct refractive errors such as myopia and hyperopia within a human eye. These techniques include, e.g., prescription glasses, contact lenses, and interventions changing the optical properties of the lens of the eye, such as refractive surgical procedures, like photorefractive keratectomy (PRK) and laser-assisted in situ keratomileusis (LASIK).

However, there is a need for a technique for determining whether a particular person has an increased risk of developing myopia, in particular, myopia caused by eye growth. In case such a "risk indicator" indicating a risk of developing myopia can be determined, early measures can be taken in order to prevent the progression of the myopia.

SUMMARY

It is therefore an object of the present disclosure to provide a technique for determining a risk indicator for myopia and, in particular, for myopia that is caused by eye growth. The risk indicator may be used for determining the risk of an onset and/or of a progression of myopia.

According to a first aspect, a system for determining a risk indicator for myopia is provided, the system comprises a wearable device configured to be attached to a body of a user (in particular, to a head of the user). The wearable device comprises at least one distance sensor configured to determine at least a first distance value indicative of a distance between the wearable device and an object located in a central vision zone of the user and a second distance value indicative of a distance between the wearable device and an object located in a peripheral vision zone of the user. The system further comprises a control unit configured to determine, based on the first distance value and the second distance value, a risk indicator for myopia.

The wearable device may be attachable to the body of the user in the broadest possible meaning. In particular, the wearable device may be attachable to the head of the user. For example, at least one attachment member may be provided for attaching the wearable device to the head or another part of the body. For example, the attachment member may be provided in the form of one or more earpieces configured to rest on an ear of the user, similar to side pieces of glasses and/or similar to a headset. The wearable device may be permanently incorporated into glasses worn by a user. Further, the attachment member may be provided in the form of one or more clipping means configured to be clipped onto an earpiece of glasses worn by the user. In this way, the "head of the user" may be understood as a head of the user including glasses (e.g., prescription glasses or sunglasses) worn by the user. While attaching to the user's head is preferable, the wearable device or a part of it can also be attached to any other location on the body of the user. For example, the wearable device can be attached to the chest of the user. In this case, the sensor(s) of the device may be directed forwards.

The distance sensor may operate according to a known technique for determining a distance. For example, the distance sensor may comprise a laser distance sensor, an ultrasonic distance sensor, an infrared proximity sensor, a radar, an imaging sensor, a camera, or any other suitable means for determining the distance value indicative of the distance between the wearable device and the object located in front of the head of the user. A camera can be a standard two-dimensional (2D) imaging camera or a range imaging camera, providing images of the distances to the objects. For example, distance values can be estimated from 2D images by recognizing objects with known geometrical dimensions and calculating distance from the dimensions on the image. A range imaging camera can implement stereo triangulation, sheet of light triangulation, decoding of structured light illumination, time-of-flight measurements, interferometric imaging or coded aperture, among others. The camera can be a light-field camera able to detect a direction of light along with intensity. The distance value may be, e.g., a length provided in the unit of meters, centimeters, or millimeters. The distance value may indicate, e.g., a distance between the eye of the user and the object. In this case, the distance value is indicative of the distance between the wearable device and the object in case the spatial relationship between the wearable device and the eye of the user is known. The distance value may indicate, e.g., a value of infinity in case no object is present in front of the head of the user or in case the next object in front of the head of the user is further away than a predefined threshold value.

In one or more embodiments, the distance sensor may be configured to measure a viewing distance of the user based on an accommodation effort of the eyes. The distance sensor can be further adapted as an eye movement senor capable of detecting movements (and/or a change of size) of the pupils. When human eyes focus on an object, they perform coordinated adjustments in vergence, shape of the lens to change optical power and, correspondingly, focal length and pupil size. For example, monitoring of positions of both eyes can allow detection of the vergence (convergence and divergence), which is a simultaneous movement of both eyes in the opposite direction to obtain or maintain binocular vision. The eyes move towards each other while focusing on near objects and move away of each other while focusing on distant objects. Changes of the shape of the lens can be monitored by tracking the reflections of the probing light from surfaces of the lens (for example, by analysing Purkinje images P3 and P4). When focusing on a near object, pupils constrict in order to minimize image blurring. Pupil size can be measured with imaging or any other suitable method. The system can detect the accommodation by detection of pupil size changes. During the detection of the accommodation, the system may compensate effects to the size of the pupil due to brightness which may be measured with the ambient light sensor.

Additionally distance to objects in a user's peripheral visual field can be measured with different sensors aligned in different directions or with devices capable of scanning multiple directions.

The control unit may comprise at least one processor and at least one memory for storing instructions to be carried out by the processor. The control unit may be configured to receive the distance value from the at least one distance sensor. In the present disclosure, when it is said that a second value is "determined based on" a first value, that means that an algorithm or a calculation rule is provided which uses the first value as an input parameter. In other words, the outcome of the determination, i.e., the second value, is influenced by the first value. In the case of the risk indicator and the first and second distance values, that means that the first distance value and the second distance value have an influence on the risk indicator (e.g., on a value of the risk indicator). However, the first and second distance values are not necessarily the only values or parameters influencing the risk indicator.

The risk indicator may be, e.g., a numerical value, wherein a higher value indicates a higher risk of myopia. Alternatively, the risk indicator may be a binary value ("0" or "1"), wherein a "0" indicates that a risk of myopia (e.g., a risk of developing myopia in a predetermined timeframe of, e.g., 1 year of 2 years) is below a predefined threshold value and a "1" indicates that the risk of myopia is above a predefined threshold value. Hence, a "1" might indicate that early measures for preventing the myopia should be considered. In the entire present disclosure, the "risk of myopia" may indicate a risk of myopia progression and/or a risk of myopia onset. For example, one and the same numerical value may be used to determine a risk of myopia onset and a risk of myopia progression. According to other embodiments, a value may be outputted for a risk of myopia onset and a different value may be output for a risk of myopia progression. In other words, the risk indicator may be a multi-dimensional (e.g., two-dimensional) risk indicator.

The at least one distance sensor may be configured to determine distance values separated/resolved in time. In other words, each distance sensor of the system may be configured to record a time series of distance values d(t). The time series may be recorded and/or stored in a memory in a way that a time (e.g., date and time) of recording the respective distance value can be assigned to the corresponding distance value, e.g., in the form of a time stamp.

In particular, for a single distance sensor configuration (i.e., the system comprises only one distance sensor) the distance sensor has to provide measurements separated in time, to provide a sequence of distance measurements (i.e., a time series of distance values). A frequency of the distance measurements should be sufficient to obtain multiple measurements during each episode of visual activity in order to facilitate statistical analysis of data. Nowadays, human attention span is significantly reduced due to mobile devices usage. It would be normal for user to switch from one activity to another several times per minute. It is thus advisable to sample the distance sensor(s) with a sub-second frequency. At the same time, due to the physical limited speed of human head and body movement it is hardly needed to sample with frequently above 100 Hz. Thus the optimal range of a distance sensor sampling frequency may be between 1 and 100 Hz. This may be applied to each distance sensor of the system and, in particular, in case the system only has one distance sensor.

Where a range of parameters are collected, the frequency of good behavior patterns (i.e., that reduce myopia risk) and bad behavior patterns (i.e., that increase myopia risk) can be analyzed to provide specific recommendations regarding changes of behavior to minimize the risk of myopia progression or onset.

The wearable device and the control unit of the system are not necessarily provided at the same physical location and/or within the same housing. For example, the control unit may be part of the wearable device. The wearable device may be provided in the form of glasses. In this case, the wearable device may comprise an output unit (e.g., in the form of a display unit) configured to output the risk indicator.

Alternatively, the control unit may be provided in the form of a separate device configured to receive output values of the wearable device and, in particular, configured to receive the distance values determined and recorded by the wearable device. For example, the wearable device may be configured to record the distance values over a predefined period and to store the distance values in the memory of the wearable device. The wearable device may comprise an interface configured to output the recorded distance values to the control unit. The control unit may comprise an input unit for receiving the distance values from the control unit. The control unit may then be configured for determining and, optionally outputting, the risk indicator.

In one or more embodiments, the control unit may be part of a cloud. In other words, the control unit may be located on one or more network severs accessible by the wearable device. The one or more network servers may be accessible via the Internet, e.g., via an encrypted connection. Hence, the evaluation of the measured distance values may be carried out by the control unit as a central control unit located on one or more cloud computing devices. Once the control unit has determined the risk indicator, the risk indicator may be signaled back to the user, e.g., to the wearable device. Further, the risk indicator may be derived from the control unit via a network interface (e.g., an Internet page secured via a login procedure), such that the user and/or a physician may have access to the risk indicator. The risk indicator may also be exclusively signaled to a physician (e.g., a treating physician of the user).

In the following, details regarding a model for determining the risk indicator by the control unit are described.

The accommodation error can be integrated in order to create a metric reflecting the risk of myopia onset and/or progression. In general, higher prevalence of accommodation error leads to a higher risk, thus the simplest model could take some statistical metric of the accommodation error distribution and relate it to the risk. The required metric can be calculated from the accommodation error (i.e. from a mismatch between the first distance value and the second distance value) in real time or system can store the history of accommodation error and thus the metrics can be calculated based on the historical data. For example, mean accommodation error in a time window of interest can used, where the time window can be an hour, a day, a week, a month, a year, etc. Storing the history of relevant parameters allows the user or healthcare provider to select different intervals for the data analysis and explore periodicity in the data, for example, by looking on the statistics in the specific times of the day, days of week or seasons.

The metric can also be a median or any other percentile. As a more simplistic measure the absolute or relative time with accommodation error above a predefined (critical) threshold can be used. For example, the system can be configured to report the number of hours with an accommodation error outside of normal range per week. In another example the system can report the time in relation to absolute time period or time of wearing/using the wearable device, for example, the system can be configured to report the percentage of time with abnormal defocus/error per selected interval.

On the next level of approximation the additional factors influencing the risk can be included in the model, such as ambient light, time spent indoor/outdoor, viewing/reading distances, time spent in different activities, geometry of the eye, demography and history of myopia in the family. These factors can enter the model independently or can attenuate the contribution of other factors, such as peripheral defocus. For example, exposure to high level of ambient light is expected to reduce effect of accommodation error due to increased depth of field of eye optics, while dim light conditions would maximize an impact of accommodation error.

In a similar way, information on the eye geometry obtained with another method allows to account for the differences in the shape of the eye. For example, peripheral hyperopic defocus is amplified in elongated eye, in contrary, in the short eye defocus in periphery is reduced.

The effect of peripheral defocus can also vary with circadian rhythms, in particular with diurnal rhythms. For example, periodical variations of axial length of the eye and choroidal thickness are influencing an impact of peripheral hyperopic with the longer eye geometry amplifying and shorter eye dampening effect of peripheral defocus. As a result the eye is more sensitive to hyperopic defocus in the early mornings and less at night. The circadian rhythms can be taken into account in the model by introducing real-time clock to the device and the time information into the model.

The model of cumulative effect of myopia risk might include a reset mechanism. It has been shown in animal studies that a short period of absence of hyperopic accommodation error (clear vision) can neutralize accumulated effect of hyperopic defocus. This effect can be taken into account by introduction of integration window, for example in the form of a leaky integrator which is slowly charging with hyperopic defocus and relatively faster discharging in the absence of hyperopic defocus.

In one implementation, a risk score can be a non-negative integer valued accumulator variable R which is incremented by first value (e.g. 1) after each complete minute of sustained hyperopic defocus (D) above a first defined threshold (D1). At the same time, each minute of hyperopic defocus below a second defined threshold D2 (lower than the first threshold D1>D2) results in a decrement of accumulator variable R by a second value, which is expected to be larger by absolute value than the first value (e.g. 5). This assumes that defocus is signed with the positive value corresponding to hyperopic defocus and negative—to myopic.

Since R is non-negative, decrementing can only bring it to the minimal value of zero, so sustained period of clear vision or myopic defocus only keep the accumulator R at minimum, which implies absence of preventive effect of clear vision or myopic defocus.

In an implementation of risk integrator variable R is real valued and non-negative and adjusted at each time step i according to the following rule:

$R(i)=f(D(i))+R(i-1)$, where $R>0$ $R(i)$ is a risk accumulator variable at time step i, $R(i-1)$ is a same variable at previous time step, $D(i)$ is real-valued hyperopic defocus and $f(D)$ is a response function.

Response function can have a shape of step function:

$f(D)=A$ for $D>D1$ (hyperopic defocus charging) and $f(D)=-B$ for $D<D2$ (clear vision and myopic defocus discharging), $f(D)=0$ for $D2 \leq D \leq D1$ (indeterminacy/insensibility zone), where $D2<D1$ are predefined threshold values and $A,B>0$ (predefined values).

The response function can be more elaborated to include linear dependence and saturation:

$f(D)=A$ for $D1'<D$ (saturation of hyperopic defocus charging)

$f(D)=\alpha(D-D0)$ for $D0<D<D1'$ (linear hyperopic defocus charging)

$f(x)=-\beta(D-D0)$ for $D2'<D<D0$ (linear clear vision/myopic defocus discharging), $f(x)=-B$ for $D<D2'$ (saturation clear vision/myopic defocus discharging), where $D2'<D0<D1'$ are predefined threshold values and $\alpha,\beta,A,B>0$ and $A=\alpha(D1'-D0)$ and $B=-(D2'-D0)$.

The response function can include linear dependence, saturation and insensibility zone:

$f(D)=A$ for $D1'<D$ (saturation of hyperopic defocus charging)

$f(D)=\alpha(D-D1)$ for $D1<D<D1'$ (linear hyperopic defocus charging)

$f(D)=0$ for $D1 \leq D \leq D2$ (indeterminacy/insensibility zone), $f(x) = -\beta(D-D2)$ for $D2' < D < D2$ (linear clear vision/myopic defocus discharging), $f(x) = -B$ for $D < D2'$ (saturation clear vision/myopic defocus discharging), where $D2' < D2 < D1 < D1'$ are threshold values and $\alpha, \beta, A, B > 0$ and $A = \alpha(D1'-D1)$ and $B = -\beta(D2'-D2)$.

Response function can have a form of sigmoid/logistic function, hyperbolic tangent, rectified linear unit, etc. or any combination.

The control unit may be configured to determine the risk indicator such that a higher mismatch between the first distance value and the second distance value leads to a risk indicator indicating a higher risk of myopia. In other words, a mathematical model employed by the control unit may consider a mismatch between the first distance value and the second distance value and in case this mismatch is high (e.g., has a value above a predefined threshold value), the risk indicator will indicate a high risk of myopia. It may be determined if the mismatch is above a predefined threshold value for a minimum number of times and/or for a minimum amount of time and, in this case, the risk indicator may be increased.

The wearable device may comprise a first distance sensor directed in a central direction towards the central vision zone of the user, wherein the first distance sensor is configured to determine the first distance value, and a second distance sensor directed in a peripheral direction towards the peripheral vision zone of the user, wherein the second distance sensor is configured to determine the second distance value.

For example in the above case, the system may be capable of sampling in a plurality of directions without reliance on device motion (i.e., without having to rely on sensor output of one or more sensors indicating a motion of the wearable device). This can be achieved with at least one additional distance sensor (i.e., the second distance sensor) oriented differently from the first distance sensor, for example downwards. This can be also achieved with the single sensor having a plurality of space or angle-resolved detection zones, as an array of detectors or as a camera (see below). The single sensor might have a plurality or probing signal sources, e.g. lasers directed in a plurality of directions for the case of time-of-flight sensors. The sensor can be designed to vary direction of source and/or detector to probe distance in different directions (active scanner). Sampling of the different directions can be performed simultaneously, like in the camera configuration, or sequentially (scanner configuration). The ability to obtain measurements with additional sensors may allow to increase a density of the sampled environment especially outside the range of head movements.

In addition to the distance to the objects in space the system might incorporate other measured parameters associated with the same orientation and/or position. For example, by including amplitude of reflected signal it is possible to enhance the data in order to increase the accuracy of objects and activities classification. For example, surface of the computer screen might have a higher reflectivity as compared with surface of the desk and thus classification algorithm can be designed to take into account requirement for the reflectivity of the object. Additionally or alternatively, the wearable device may comprise a light intensity sensor as a part of the distance sensor or a separate sensor co-directed with the distance sensor and used to detect light intensity and spectral content in the viewing direction. For example, handheld mobile devices, such as mobile phones or handheld computers/tablets, computers, terminals, television sets, etc. are typically using actively illuminated displays. The light intensity sensor can be configured to recognize light emitted by those objects from intensity, spectral content, flickering pattern (frequency and intensity) or other light properties. Light intensity sensor measurements may be aligned with orientation and/or position measurements and mapped in to the representation of environment in order to support classification of activities performed by the user and recognition of environment (such as indoor or outdoor). Combining light property measurements with distance measurements can further improve classification. Generally said, an output of a light intensity sensor may be used for determining the risk indicator (i.e., may have an influence on determining the risk indicator).

The distance sensor may comprise a camera having a field of view including the central vision zone and the peripheral vision zone, wherein the distance sensor is configured to determine the first distance value and the second distance value based on one or more images captured by the camera. For example, the control unit may be configured to analyze a time series of images captured by the camera and to determine, based on the time series, the first distance value and the second distance value. The camera may comprise a plurality of sub-cameras each having a sub-field of view, wherein a combined field of view (i.e. a combination of the sub-fields of view) is including the central vision zone and the peripheral vision zone.

The distance sensor may comprise an eye activity sensor capable of measuring viewing distances from accommodation effort of the eyes, e.g., from vergence eye movement, pupil adjustments, and/or lenses changes, among others. In this case the first distance value and second distance value may be determined from the time series of viewing distances. For example, viewing distance determined during periods of fixation may correspond to the central vision zone (first distance value), while viewing distance during periods outside of fixation may correspond to the peripheral vision zone (second distance value). Additionally or alternatively, the vision zones can be identified from the eye directions. The gaze direction can be derived by combining eye direction with head orientation estimated from orientation sensors. By combining viewing distance measurements with the gaze direction it is possible to reconstruct geometry of environment in relation to user's head and with this estimate peripheral defocus.

In the case a plurality of distance sensors are provided, each distance sensor may—at the same time—provide one distance value, e.g., indicating a distance between the respective distance sensor and an object to which the distance sensor is directed. In the case that one distance sensor determines a plurality of distance values, this distance sensor may be configured to scan a laser beam in a predefined angular range or this distance sensor may comprise a camera for providing a two-dimensional image with the ability of processing the two-dimensional image to determine the plurality of distance values. Further, the distance sensor may comprise at least two cameras for determining a two-dimensional image by each camera, wherein the two-dimensional images are processed to determine the plurality of distance values. The peripheral direction may have an angle of at least 5°, at least 10°, at least 20°, at least 30°, or at least 45° with regard to the central direction. For example, the peripheral direction may be directed downwards and/or to a side with regard to the central direction.

In case more than one second distance value is determined, more directions may be considered, which may increase the accuracy of the system. For example, at least one vertical second distance value may be determined for a direction vertically departing from the first direction and at least one horizontal second distance value may be determined for a direction horizontally departing from the first direction.

By analyzing the first distance value and the second distance value, a chance of appearance of a peripheral defocus and/or a degree of a peripheral defocus may be determined.

The control unit may be configured to identify the first distance value during a period of fixation, when a variability of distance measurements of the distance sensor is below a first predefined threshold during time intervals exceeding a second predefined threshold and the second distance value is identified outside of the period of fixation.

The variability may comprise or may correspond to at least one of a number of times the measured distance value changes from a value below a first predefined threshold value to a value above a second predefined threshold value within a predefined period, a number of times a time derivative of the measured distance value changes its sign within a predefined period, a difference between a maximum value of the measured distance value and a minimum value of the measured distance value within a predefined period, and a maximum of a time derivative of the measured distance value within a predefined period.

However, the temporal variability should not be limited to the above examples, which represent a list of mathematically and clearly defined ways of determining the temporal variability. Other ways of determining the temporal variability may exist, which are also covered by the present disclosure.

As described above, the control unit may be configured to identify periods of fixation, i.e., when the user is focusing on a main object of visual activity, typically aligned in the central vision zone, and identify deviations from main visual activities, which yield distances to the surrounding objects, which are otherwise located in the peripheral vision zone. For example, when the user is watching TV, the user's fixation is expected to be on the TV and the distance sensor would primary report distances to the TV screen. However, due to the natural head movement or distractions, the user would occasionally turn his or her head towards the objects in the periphery (i.e., in the peripheral vision zone), for example, objects in the hands of the user, such as a snack or a remote control. In another example, a user working on a desktop personal computer would be mainly focusing on the computer display and occasionally turn the head towards a keyboard or other objects on the desk. The algorithm implemented by the control unit can be configured to statistically differentiate a period of fixation as a period of low variability of distance measurements, for example, identified by a standard deviation below a predefined threshold and, correspondingly, associate measurements fallen outside of the range as outliers, associated with objects outside of the main visual activity (i.e., objects in the peripheral vision zone).

The distance sensor may be capable of providing additional metrics associated with the distance signal, for example, the amplitude of the signal and/or other quality metric. In this case the additional metrics can also be used to differentiate measurements from the primary objects of visual activity (i.e., objects in the central vision zone) and objects in visual environment (i.e., objects in the peripheral vision zone). For example, the distance measurements might be based on the detection and characterizing the pulse sent towards objects and reflected back (such as ultrasonic sensors and laser time of flight sensors). In this case the distance sensor may also be capable of measuring an amplitude of a reflected pulse. In the example above, reflections from the computer screen might yield pulse amplitude different from the amplitude of reflections from environment, which can be included in the signal analysis.

Further, the wearable device may comprise a motion sensor, and the control unit may be configured to identify periods of fixation as periods with a motion below a first predefined threshold during time intervals exceeding a second predefined threshold and to identify the first distance value during one of the periods of fixation and to identify the second distance value outside of the periods of fixation. Hence, an output of the motion sensor may define, which of the measured distance values (e.g., of a time series d(t)) of a distance sensor are first distance values and which of the measured distance values are second distance values.

The wearable device may include exactly one distance sensor for determining exactly one distance value at a given time, such that the exactly one distance sensor is configured to determine the first distance value and the second distance value at different times.

For example, the exactly one distance sensor may be directed in only one direction and, therefore, may only determine a distance between the wearable device and an object positioned in said direction. The expression "exactly one distance value at a given time" means that not more than one distance values are determined simultaneously. However, different distance values may be determined at different times. For example, a wearable device may be provided which only includes one distance sensor pointing in a direction of a central axis of the wearable device. Alternatively, the exactly one distance sensor may point in a direction away from the central axis of the wearable device, into the peripheral vision area.

The control unit may be configured to determine, based on an output of the exactly one distance sensor, the first distance value and at least one second distance value.

The control unit may be configured to determine an accumulated duration in which the mismatch between the first distance value and the second distance value is above a predefined threshold value within a predetermined period, and to determine the risk indicator such that a higher accumulated duration leads to a risk indicator indicating a higher risk of myopia.

In this way, a fraction of time may be determined in which a peripheral defocus exists. The higher this time fraction is, the higher the risk of myopia may be.

The wearable device may comprise at least one additional sensor configured to output additional sensor data, wherein the control unit is configured to determine, based on the additional sensor data and based on an output of the at least one distance sensor, the first distance value and the second distance value. The additional sensor may comprise at least one of an orientation sensor for determining an orientation of the wearable device, a position sensor device for determining a position of the wearable device and an acceleration sensor for determining an acceleration of the wearable device.

The acceleration sensor may be configured to detect an amount of motion of the user. Hence, the acceleration sensor may also be referred to as motion measurement sensor. During periods of fixation it is typical for the user to reduce an amount of body and head motion in order to maintain the optimal quality of image perceived by the eyes. Episodes of distractions on another hand are characterized by the deviation from the original direction of fixation, which are reflected in a motion signal of the acceleration sensor. Thus the additional sensor data and, in particular, the motion signal can serve as an additional or primary signal for identification of fixation and deviation periods. In other words, the control unit may be configured to determine a period of fixation based on the additional sensor data.

It is also understood that in case of moving a visual target, for example, while watching objects passing by, the user tends to move the head during fixation. This can be accounted for in the signal processing by differentiating pursuit distance and/or head motion and deviation signals.

Additionally or alternatively, the wearable device may incorporate at least one of an orientation sensor and position sensor. Combination of such sensors with distance measurements allows to map the measured distances to the geometry of the environment. In the example above, while fixating on the computer screen the user will maintain a first direction of the sensor and during intermittent deviations to desk surface or other surrounding objects, the head of the user would naturally lean downwards or sideways, which can be detected by the orientation sensor. The control unit can be configured to detect a primary orientation of the system (for example, straightforward during fixating on computer screen) and differentiate it from secondary orientations during deviation from primary vision activity (e.g. while looking downwards). Such detection can be made with statistical processing of the orientation signal and detection of the episodes of stable orientation when statistical dispersion/variation of orientation is below predefined threshold. Statistical dispersion can be quantified with variance, standard deviation, interquartile range, inter-percentile range, statistical range (spread between minimum and maximum), mean absolute difference or any other statistical measure of dispersion. The primary orientation can be detected with statistical measures of central tendency of orientation distribution, such as arithmetic mean, median, mode or other measure. Distance measurements obtained in system orientation corresponding to primary orientation are associated with central vision zone and mostly responsible for accommodation response. Episodes of deviation can be detected as periods when orientation is deviated significantly from the center of distribution, for example, when the absolute difference between current orientation and primary orientation is above predefined limit. Distances measured during such episodes correspond to peripheral vision zone and thus typically correspond to accommodation demand of peripheral vision.

With sufficient amount of samplings due to the natural head and body movement of the user it may be possible to obtain distance scans of the environment from measurements taken in a range of different directions in relation to the head position. For example, measurements of the accelerometer allow to relate orientation of the device to a gravitational field (pitch angle). Using a magnetometer allows to relate orientation to a magnetic field (yaw and pitch angles), which may be related, with correct calibration, to the magnetic field of the Earth. A combination of those sensors and, optionally, a gyroscope sensor, allows estimating an absolute orientation of sensor in three-dimensional space. Such combination of three-axis accelerometer, three-axis magnetometer and three-axis gyroscope are referred to as absolute orientation sensor.

In a way, similar to the orientation detection described above, the wearable device may be equipped with at least one position sensor to detect transverse displacement of the wearable device and relate them to the measurements of distance in order to differentiate periods of fixation and diversion. The position sensor in combination with distance measurements allows to scan the environment due to the natural movement of the user. The position sensor can be implemented by measuring acceleration detected by an accelerometer in order to estimate a relative displacement or it can be implemented from distance measurements to nearby anchor nodes with known fixed position, such as radio-frequency emitting devices, like mobile phones, internet access points or Bluetooth beacons. The position sensor may be a geolocation sensor.

The position sensor may be combined with an orientation sensor to further improve scanning of the environment represented as a point cloud—i.e., a set of data points in space. The point cloud can be used to recognize objects in space and/or recognize user's activities in order to separate distance to the objects in the central viewing zone from distances to objects in the peripheral viewing zone and thus calculate the peripheral defocus and risk indicator.

For example, a head movement of the user may be detected, e.g., by means of a movement sensor (e.g., an accelerometer, a gyroscope, and/or a magnetometer). Based on an output of the movement sensor, a direction may be derived, into which the head of the user is directed. Based on this direction, it may be determined whether a currently detected distance value corresponds to a first distance value (e.g., pointing in a central direction of the wearable device) or to a second distance value (e.g., pointing in a peripheral direction of the wearable device). Based on the movement sensor, it may be determined that the user has only rotated and not translocated the head to another location.

The control unit may be configured to determine the risk indicator by making use of biometric information indicative of a shape of an eye of the user, wherein the biometric information is used to determine an amount of peripheral defocus of light beams coming from the second direction.

For example, a more elongated eye may suffer a higher peripheral defocus since the difference (i.e., the distance) between central and peripheral zones is larger within a more elongated eye as compared to, e.g., an eye having a substantially spherical shape. This knowledge may be suitably considered in the process of determining the risk indicator.

The first distance value may be measured along a central axis of the wearable device and the second distance value may be measured along a peripheral direction with regard to the central axis.

The central axis of the wearable device may be aligned with a viewing direction of the eye of the user when the user looks straight ahead. In other words, the central axis of the wearable device may be aligned with a viewing direction of the eye of the user when the user looks at a point at the horizon which is positioned directly in front of him/her. In case the wearable device comprises temples, the central axis may be substantially parallel to an extension direction of the temples. The peripheral direction may be a direction tilted downwards and/or to the side with regard to the central axis.

The wearable device may comprise an eye tracking device for determining a viewing direction of an eye of the user. The control unit may be configured to determine, based on the determined viewing direction and based on an output of the at least one distance sensor, the first distance value for indicating a distance to an object located at an optical axis of the eye and the second distance value for indicating a distance to an object located at a peripheral direction forming a predefined angle larger than zero with respect to the optical axis of the eye.

Hence, in case an eye tracking device is used, the control unit does not rely on the assumption that the first direction of the wearable device corresponds to the viewing direction of the user but rather the real viewing direction of the user may be considered for determining the first distance value and the second distance value.

The wearable device may further comprise a light sensor for determining a light intensity and/or spectral content, and the control unit may be configured to determine the risk indicator based on the light intensity and/or spectral content.

The wearable device may incorporate the light sensor and/or a color sensor co-directed with the distance sensor. Measurements of light can be used to improve a classification of objects and/or activities. For example, screens of mobile devices, computer screens and display panels in general are typically actively lid and act as light sources. The ability to detect light of those devices allows to increase a sensitivity and specificity of classification. For example, including the light sensor co-directed with the distance sensor can help to differentiate reading a book or reading from a tablet, since the latter would comprise a light source while former would not. The ability to obtain periodical sampling of light intensity allows to adapt the system to detect a temporal component of illumination, which can be used to differentiate types of media presented on a display. For example, dynamic media, such as video or game would have variable intensity and spectral content due to the frequent changes in displayed visuals of the color and intensity content can be used to recognize such content. In contrary, an electronic book reader or a book app would have a relatively stable visual representation between page turns since any dynamic changes would interfere with reading activity. Thus, the control unit may be configured to determine an activity based on an output of the light sensor.

Additionally or alternatively, the wearable device might incorporate an ambient light sensor designed to measure an intensity and/or color content of environmental light. It can be aligned in the same direction as the distance sensor or in a different direction, for example upwards. The ambient light sensor directed upward would be able to measure light from light sources, which are typically located above the user's head, such as sun, skies, cell lightning, street lamps, etc. The ambient light sensor might have a channel designed to detect ultraviolet light. Environmental light conditions may have important influence on the risk of myopia progression. High illumination condition leads to the pupil constriction of the user which increases the depth of field of image on the retina and reduces the effect of peripheral defocus. In contrary, low illumination leads to dilated pupil and decreased depth of field of the image and thus maximizes the effect of peripheral defocus. Thus illumination conditions can be included in the model of determining the risk indicator, such that the risk indicator indicates a higher risk of myopia in case a lower amount of illumination is detected by the light sensor.

The light sensor, e.g., in the form of an ambient light sensor can be used to differentiate indoor and outdoor settings. Such differentiation is an important factor in myopia risk, since it has been shown that time spent outdoor has a protective effect against myopia progression.

Since the illumination level indoors rarely reaches the level of outdoor light during day, the simplest detection can be performed by comparing ambient light level with a predefined threshold and reporting outdoor context when ambient light is above threshold and indoor—otherwise. A sensor sensitive in the ultraviolet spectral region is expected to be more specific due to the typical absence of artificial UV light sources in the normal indoor environment, while it is unavoidable in the daily outdoor settings. The threshold can also be adjusted based on the time of the day, season and geolocation: longitude, latitude and altitude to account for variation of expected outdoor illumination conditions. For example, during night hours logic based on illumination threshold would not work for the reasons of absence of sun as a light source, which would be accounted by information on sun phase estimated from location and date/time. Thus, it can be determined whether an output of the light sensor is above a predefined threshold value and, based on this, it can be decided whether the user is in an indoor or outdoor environment.

Another implementation can use a flickering detection of light. It is known that the light from screens and some modern artificial light sources are modulated. It is possible with the capable device to detect periodic fluctuations of intensity and with this to detect presence of artificial light sources and with this recognize the indoor/outdoor context.

Thus, the light sensor may be used to identify a type of activity of the user and/or an environment in which the user is currently located.

Other sensors can be used to differentiate outdoor/indoor settings, for example, the distance sensor. Since the range of viewing distances in a typical indoor environment is limited by the walls and ceiling it is possible to detect the indoors environment from the statistics of viewing distances, for example by comparing with a threshold.

Distances between the walls might have high variability, while distance to the ceiling in the typical building is more consistent. Thus it is beneficial to include an orientation sensor into consideration in order to detect presence of the ceiling and distance to it when system is directed upwards. In an implementation, the wearable device might include a distance sensor tilted upwards or completely oriented vertically upwards. With this device presence of a ceiling can be reliably detected and attributed to an indoor environment.

In an implementation the characteristics of peripheral defocus, which is a deviation of central and peripheral distances can be used for the detection of an indoor environment. It is known that typical indoor environment induced much higher peripheral defocus in comparison with outdoor environment and thus measurements of peripheral defocus can be used as a signal for differentiation of indoor/outdoor settings separately or in combination with other signals.

To summarize the above, for example, a higher illumination level may lead to the assumption that a pupil size of an eye of the user is reduced, which reduces the extent of the peripheral defocus due to the increased depth of focus caused by the smaller pupil size. Therefore, the risk indicator might be determined such that a higher illumination level over a larger amount of time leads to a risk indicator indicating a smaller risk of myopia. More elaborated implementation may include modelling of the pupil size as a function of measured scene luminance or overall illumination level. Pupil size may be included into the model of the peripheral defocus calculation in the eye model using ray tracing.

The control unit may further be configured to determine the risk indicator based on a type of activity detected by the wearable device.

Possible types of activities may include, amongst others, sports, reading a book or a newspaper, looking at a computer display, looking at a display of a smartphone, etc.

These activities may be determined by one or more suitable sensors, e.g., the at least one distance sensor.

Additionally or alternatively, one or more additional sensors may be provided for determining the type of activity, such as, e.g., a camera and/or a movement sensor (such as an accelerometer) or a combination of multiple sensors.

Visual activities detected with the disclosed system can serve as a factor in the myopia risk estimation. For example, time spent working with electronic display devices ("screen time") can enter the model directly as a factor contributing to the increase of the myopia progression risk. As another implementation, the library/database of peripheral defocus/accommodation error during the activities can be used to estimate the accumulated value of peripheral defocus. For example, by detecting periods of working on the personal computer, system can use typical model of visual environment for personal computer and indirectly estimate peripheral defocus. This can be also done in combination with the actual measurements of the environment in order to enrich data. The viewing distance measured with the distance sensor can also be included in the model of the risk. For example, short working distances, as with small phones, or reading close up is a recognized risk factor. Therefore, the risk indicator might be determined such that a statistical metric (mean, median, momentum, time, etc.) of working distances employed by the user corresponding to shorter working distance over a larger amount of time leads to a risk indicator indicating a higher risk of myopia progression.

The control unit can also be configured to evaluate a validity of the currently sampled environment/context/activity. For example, the system could have sufficiently sampled the environment while the user was working on a computer and is capable to differentiate primary and secondary orientations and/or locations. When the user is switching to another activity, such as, for example, turning towards a colleague and engaging into the discussion or standing up and walking to a coffee machine, the environment is completely changing and algorithmic representation may have to be reset. The system can be configured to evaluate validity by comparing measurement during fixation and/or during deviation. For example above, when the user turns away from a screen of the computer towards the colleague, the primary distance will change from the standard computer screen distance (e.g. 0.6-0.8 m) to the distance towards the counterparty, which is typically in the range of social distance among colleagues, which starts from 1.2 m. By detecting a sudden switch of primary distance it is possible to detect a context change and to initiate a reset of the collected statistics. Context switch can also be detected with the help of additional sensors, such as an orientation and/or a position sensor by detecting a significant change in the orientation or position of the wearable device. A motion sensor can serve as a context reset trigger by detecting a sudden significant movement of the system, for example, when the user stands up and walks away, it is associated with significant change motion signature. As mentioned previously, visual fixation is typically associated with the reduced head and body motion, since motion can distort the visual function.

The wearable device may comprise the control unit. In this case, the system may be embodied by a wearable device, wherein both the detection of the distance value(s) and the further processing of the distance value(s) are performed within one and the same device. In this case, the wearable device may comprise an output interface for outputting the determined risk indicator. The risk indicator may be outputted, e.g., to the user and/or to a treating physician of the user. Based on the outputted risk indicator, the physician can decide whether particular measures are necessary to prevent an onset/progression of myopia.

According to a second aspect, a method for determining a risk indicator for myopia is provided. The method comprises determining at least a first distance value indicative of a distance between a wearable device attached to a body of a user (in particular, to a head of the user) and an object located in a central vision zone of the user and a second distance value indicative of a distance between the wearable device and an object located in a peripheral vision zone of the user. The method further comprises determining, based on the first distance value and the second distance value, a risk indicator for myopia.

Each of the details described above with regard to the system of the first aspect may also apply to the method of the second aspect. More precisely, the method of the second aspect may involve one or more of the additional steps/capabilities described with regard to the above-discussed system of the first aspect.

According to a third aspect, a computer program product is provided. The computer program product comprises program code portions to perform the steps of the method of the second aspect when the computer program product is executed on one or more processing devices.

The computer program product may be stored on a computer-readable recording medium. In other words, a computer-readable recording medium comprising the computer program product of the third aspect may be provided.

BRIEF DESCRIPTION OF THE DRAWINGS

Embodiments of the technique presented herein are described below with reference to the accompanying drawings, in which.

In the following, but without limitation thereto, specific details are expounded in order to give a full understanding of the present disclosure. It is clear to persons skilled in the art, however, that the present invention can be used in other embodiments, which can differ from the details expounded in the following.

Figure 1:
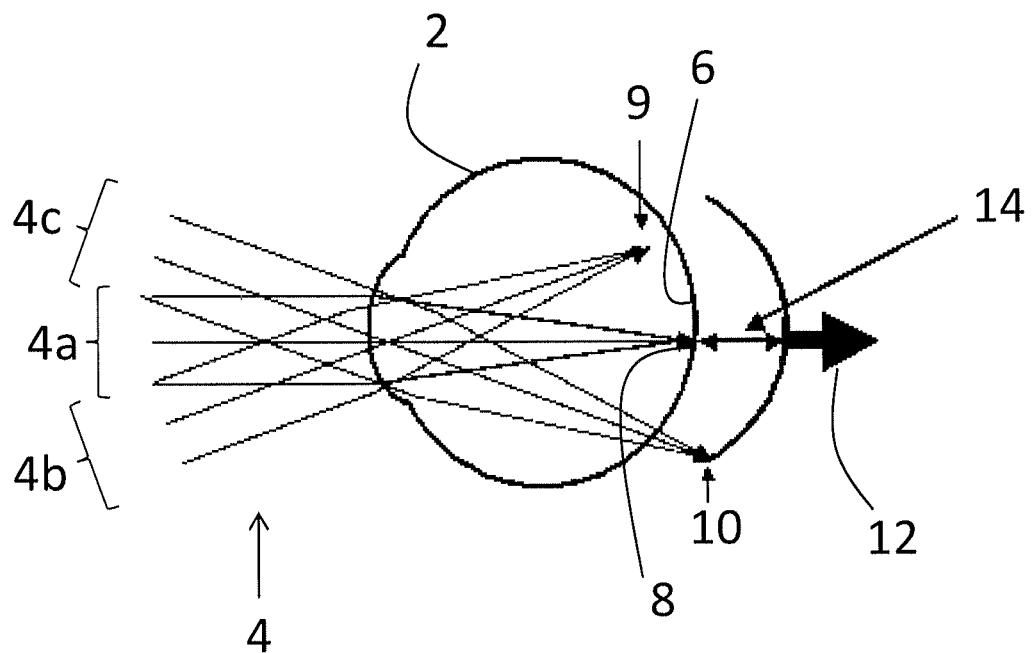
FIG. 1 shows a schematic cross section of an eye of a user for explaining different potential causes of myopia with regard to three focal points.

FIG. 1 shows a schematic representation of a cross-section of an eye 2 of a user. In the following, possible causes for myopia will be discussed with reference to the eye 2 shown in FIG. 1. It should be noted that the representation of FIG. 1 does not necessarily show one particular point in time but rather different situations are indicated within the same figure for explanatory purposes.

As shown in FIG. 1, light rays 4 are entering the eye 2 from the left side. The light rays 4 pass the pupil of the eye 2 and are focused by the lens of the eye 2 (both pupil and lens not shown in FIG. 1). In an ideal case, i.e., in order to obtain a sharp image, the light rays 4 are focused onto the retina 6 of the eye 2. This case is shown in FIG. 1 with regard to the light rays 4a forming a focal point 8 on the retina 6. In case a focal length of the lens of the eye 2 is too short (or the lens of the eye 2 is currently out of focus or focused on another object), the light rays 4 are focused in a region in front of the retina 6 and, thus, within the eye 2, as shown at focal point 9 in FIG. 1 with regard to the light rays 4b. The focal point 9 is also called a myopic defocus or may be seen as the result of a myopic defocus of the eye 2. In case a focal length of the lens of the eye 2 is too long (or the lens of the eye 2 is currently out of focus or focused on another object), the light rays 4 are focused in a region behind the retina 6 and, thus, outside the eye 2, as shown at focal point 10 in FIG. 1 with regard to the light rays 4c. The focal point 10 is also called a hyperopic defocus or may be seen as the result of a hyperopic defocus of the eye 2.

With regard to FIG. 1, causes of myopia (nearsightedness) may be explained. The following discussion is particularly relevant for children and for myopia caused by growth of the eye 2. When the eye 2 is too large (i.e., has grown too large), the image is formed in front of the retina 6 as discussed above with regard to the myopic defocus 8. However, the eye growth is triggered by the existence of a hyperopic defocus 10 (i.e., when the image is formed behind the retina 6), see FIG. 1.

As explained below, mechanisms exist that an ongoing eye growth is triggered even though the eye 2 is already grown too large and, therefore, the eye 2 is already myopic. One effect that might cause this phenomenon, is referred herein as a "spatial component".

Spatial component: An accommodation control mechanism is designed to bring the image in focus in the central zone around the fovea of the retina 6. Obviously, an image on the retina 6 is formed also in a peripheral zone surrounding the central zone. There is data that shows that the peripheral defocus 10 is also causing eye growth. In the modern indoor environment, if a person (in particular, a child) is looking at a far object, e.g., a television screen, there are high chances that, at the same time, there are other objects positioned nearby (like a desk, a screen, a book, etc.) which are positioned in peripheral directions and which are projected behind the retina 6 forming a hyperopic defocus 10 since the eye 2 is not accommodated with regard to these objects. Also this hyperopic defocus 10 is able to trigger eye growth which might cause myopia.

The hyperopic defocus 10 has been identified as one of the major risks for the development of myopia. As explained above, while the eye 2 brings the image in a central zone in focus, the peripheral zone (surrounding the central zone) might be not in focus. This effect might be exaggerated with eye growth, which elongates the eye 2. In this case the peripheral zone is even closer to the lens than the central zone and thus the image is in hyperopic defocus (or "peripheral defocus"). The eye 2 may respond to hyperopic defocus which might firstly lead to choroid thinning followed by the eye growth (elongation), which in its term leads to the further mismatch between the images in central and peripheral zones. This may create a vicious cycle of eye growth. Some researchers indicate that the peripheral zone is even a stronger trigger of the eye growth than the central zone.

Environmental factors affecting the peripheral defocus are the unavoidable presence of objects in the periphery of the vision of people. While a person might be focusing on objects in the far or at intermediate distances, there are often other objects located closer to the head of the person. Those objects, while not being in the central vision zone, would be focused behind the retina 6 and thus cause hyperopic defocus.

As shown in FIG. 1, the above mechanism triggers eye growth indicated by the thick arrow 12. As a result of this eye growth, a myopic refractive error increases as indicated by the double-sided arrow 14 in FIG. 1.

To summarize the above, a hyperopic defocus (i.e., the image is formed behind the retina 6) may stimulate eye growth (in particular, in the growing eyes of children).

Hyperopic defocus is typically caused by insufficient accommodation of the natural lens of the eye 2. A natural mechanism stimulates the eye growth, which moves the retina 6 backwards and brings the image in focus on the retina 6. In an ideal situation, when the eye 2 is already myopic, the defocus is myopic and, therefore, does not trigger the eye growth. However, as discussed above, there are situations, when this mechanism is triggered even in myopic eyes, which leads to the unwanted effect of a further eye growth. As explained above, one effect is directed to the defocus in a peripheral zone of the eye 2 (spatial inhomogeneity or spatial component).

It may thus be important to understand the working and living environment of a user to characterize the risk of the myopia development and progression based on the factors of peripheral (hyperopic) defocus. According to the present disclosure, a "peripheral defocus" refers to a hyperopic defocus in a peripheral region of the retina 6 of the eye 2.

Figure 2:
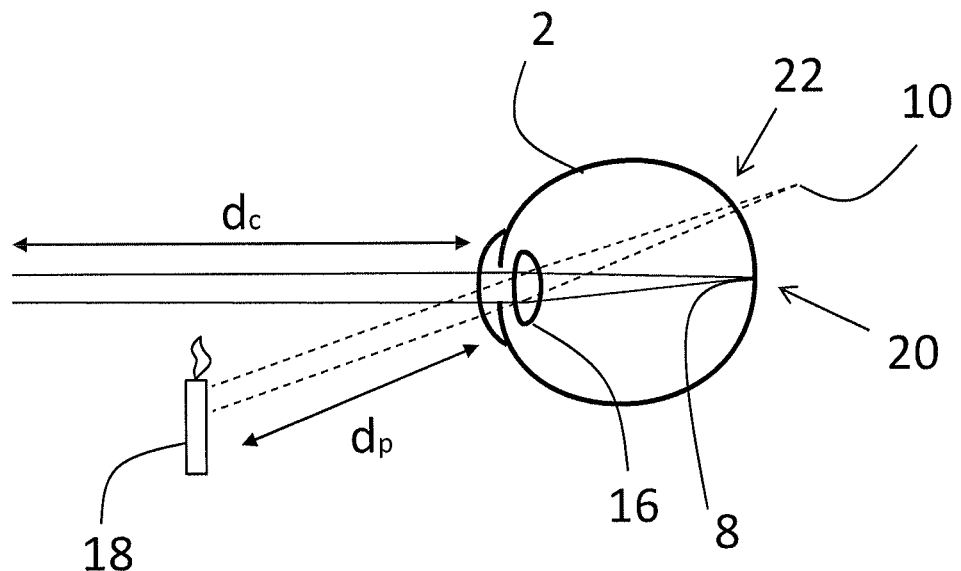
FIG. 2 shows a schematic cross section of an eye for explaining the effect of peripheral defocus.

FIG. 2 shows a representation similar to FIG. 1, wherein the occurrence of a hyperopic defocus 10 is shown. The representation of FIG. 2 shows a cross-section through a vertical plane and, therefore, a side view of the eye 2. The lens 16 of the eye 2 is focused on an object (not shown) provided at a distance $d_c$ (central distance), which might also be, e.g., infinity. As shown in FIG. 2, an image of the far object is formed at a regular focal point 8 on the retina. However, a further (nearby) object 18 is present in front of the head of the user at a distance $d_p$ (peripheral distance), which is a candle in the example shown in FIG. 2. Since the lens 16 of the eye 2 is not accommodated to the nearby object 18, an image of the nearby object 18 is formed at a hyperopic defocus point 10, i.e., in a region behind the retina. Therefore, an object 18 positioned close to the eye 2, while another object positioned far away is focused by the lens 16, may cause a hyperopic defocus and thereby myopia (in case this situation occurs often and/or over a long period).

Figure 3:
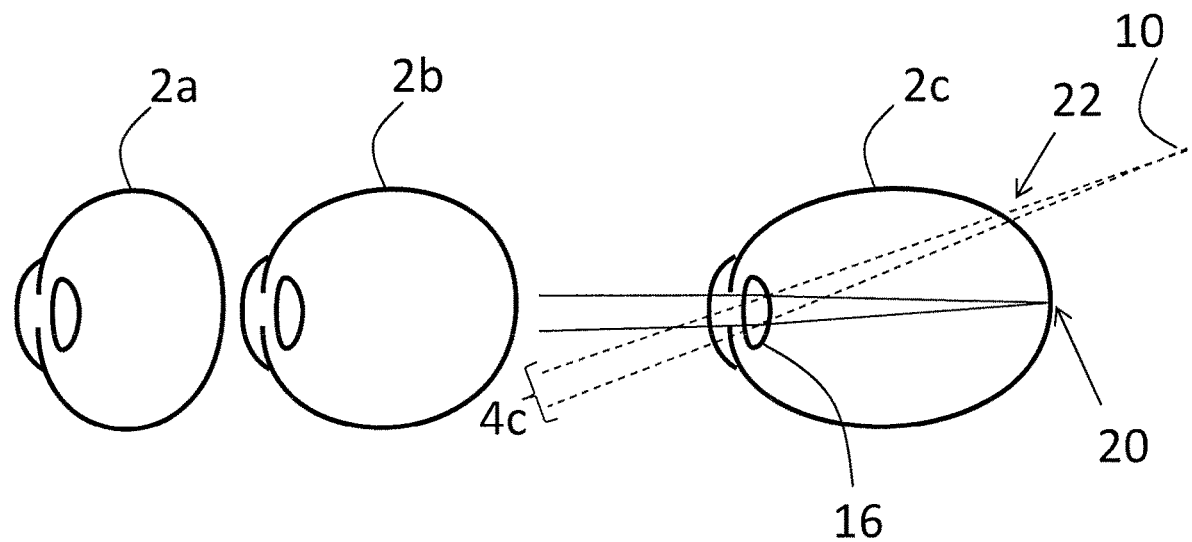
FIG. 3 shows a schematic cross section of three eyes having different shapes and the effect of a peripheral defocus on these eyes.

FIG. 3 shows how a shape of the eye 2 may have an influence on the appearance of a hyperopic defocus 10. In the left part of FIG. 3, an eye 2a is shown which has a shortened length along its optical axis. In the middle part of FIG. 3, an eye 2b is shown which has a normal length. The right part of FIG. 3 shows an elongated eye 2c which may be the result of a too strong eye growth. As shown with regard to the eye 2c, a central zone 20 (i.e., a zone where an optical axis of the eye 2c intersects the retina) is relatively far away from a peripheral zone 22 of the retina having a predefined angular distance with regard to the central axis (horizontal axis passing through the middle of the lens 16 in FIG. 3). For example, the peripheral zone 22 of the eye 2c may be in a region where the light beams 4c intersect the retina. As can be seen from a comparison of the eyes 2a and 2c, in the elongated eye 2c, a central zone 20 and a peripheral zone 22 are relatively far away from each other, which enhances the effect of peripheral defocus.

Figure 4:
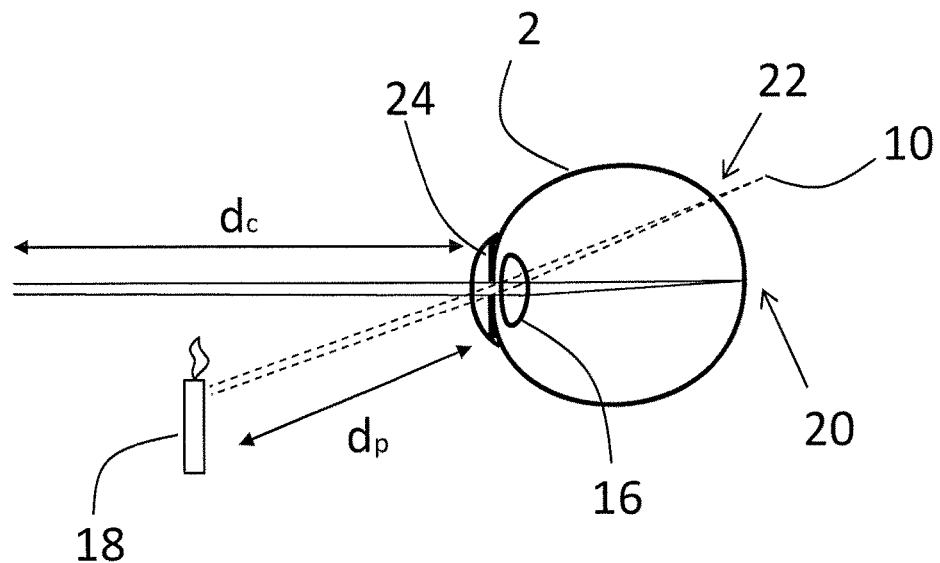
FIG. 4 shows a schematic cross section of an eye with a reduced pupil size and the effect of the reduced pupil size on the peripheral defocus.

In FIG. 4, the effect of a reduced pupil size on the occurrence of a peripheral defocus is shown. As shown in FIG. 4, a high amount of ambient light causes the iris 24 of the eye 2 to reduce the pupil size. Due to the increased depth of focus, the extent of the peripheral defocus is reduced.

In the following, examples will be described how the above observations are used by the technique of the present disclosure in order to determine a risk indicator for myopia.

Figure 5:
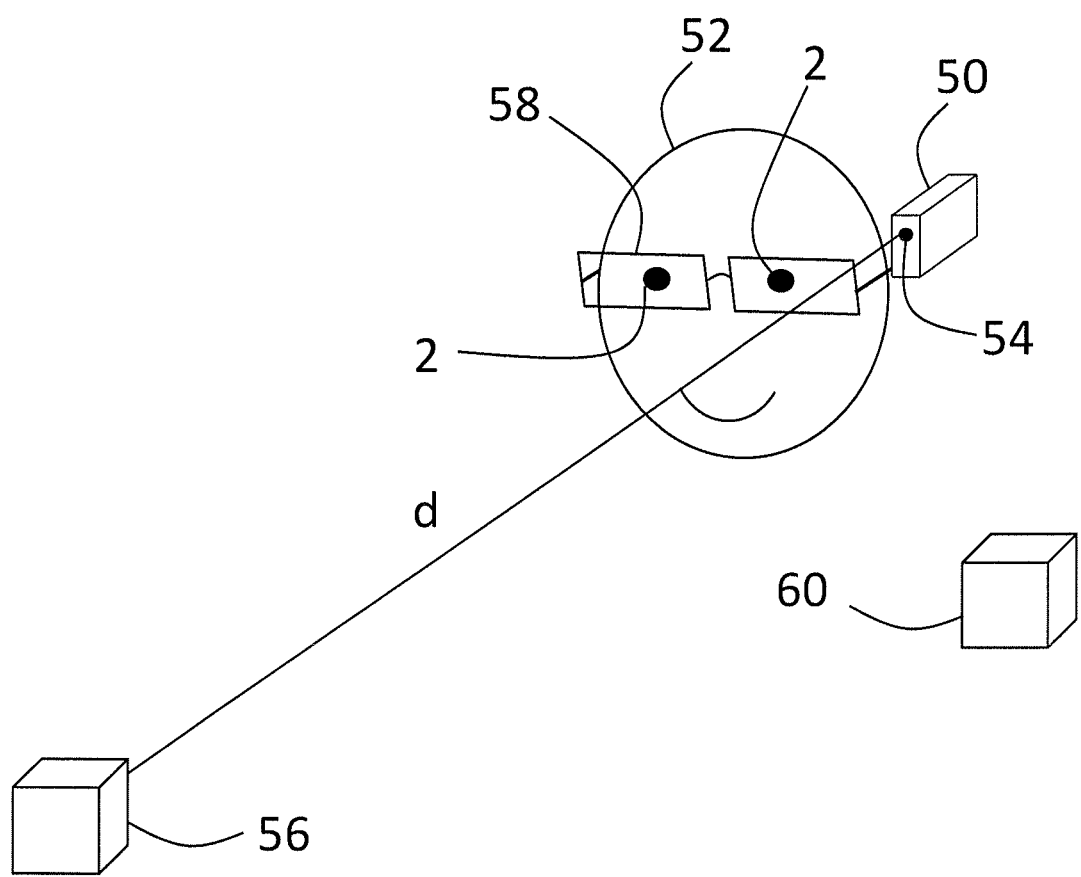
FIG. 5 shows a first embodiment of a wearable device with one distance sensor for determining a risk indicator for myopia.

FIG. 5 shows a wearable device 50 according to a first embodiment of the present disclosure. The wearable device 50 is attached to a head 52 of a user. More precisely, the wearable device 50 is attached to a frame 58 of prescription glasses worn by the user, e.g., by means of clipping means via which the wearable device 50 is clipped to a temple of the frame 58. However, also the combination of wearable device 50 and frame 58 may be regarded as wearable device according to the present disclosure, wherein according to this point of view, the wearable device 50, 58 is attached to the head 52 of the user by means of the temples of the frame 58. Instead of the prescription glasses, the frame 58 may be a frame of sunglasses, a frame with plano lenses without optical power, or an "empty" frame without lenses.

The wearable device 50 comprises a distance sensor 54 for time-dependently measuring a first distance value d(t) representing a distance between the wearable device 50 and an object 56. When the present disclosure states that a time-dependent distance value is measured, this means that a plurality of individual values are measured (d(t=$t_1$), d(t=$t_2$), d(t=$t_3$), etc.), one after the other, and stored, optionally in association with a time stamp. Therefore a suitable sampling of the distance sensor 54 is implemented. A sampling frequency of the distance measurements should be sufficient to obtain multiple measurements during each episode of visual activity in order to facilitate statistical analysis of data. Nowadays, human attention span is significantly reduced due to mobile devices usage. It would be normal for user to switch from one activity to another several times per minute. It is thus advisable to sample the distance sensor(s) 54 with a sub-second frequency. At the same time, due to the physical limited speed of human head and body movement it is hardly needed to sample with frequently above 100 Hz. Thus the optimal range of a distance sensor sampling frequency may be between 1 and 100 Hz. This may be applied to the distance sensor 54 of the present embodiment but also for the other distance sensors of the wearable devices described herein.

For measuring the distance value d(t), the wearable device 50 may employ a known technique, such as a laser distance meter, an ultrasonic distance meter, etc. As shown in FIG. 5, the distance sensor 54 points in the first direction, i.e., it is directed to the first direction. In other words, the distance sensor 54 is configured to measure a distance value d(t) along the first direction (indicated by the line in FIG. 5) to an object 56 located along the first direction. The distance value d(t) is measured such that it indicates a distance between the wearable device 50 and the object 56, wherein it is also possible to measure the distance value between the object 56 and an arbitrary reference point having a fixed spatial relationship with the wearable device 50 (e.g., a reference point where one of the eyes 2 of the user is usually located).

As shown in FIG. 5, the first direction, in which the distance value d(t) is measured, corresponds to a central direction along a central axis of the wearable device 50. The central axis may be defined as a direction along a viewing direction of the eyes 2 of the user, when the wearable device 50 is worn on the head 52 of the user and when the user looks straight ahead (e.g., at a point on the horizon). The central direction substantially corresponds to a direction of extension of the temples of the frame 58.

In the embodiment of FIG. 5 it is assumed that the first direction corresponds to a viewing direction of the user. This assumption is a good approximation since it has been shown that users usually turn their head 52 in the viewing direction, such that the viewing direction and the central axis of the eyes usually correspond to each other.

The distance sensor 54 measures a time-dependent distance value d(t). The distance value d(t) represents a distance along the central axis of the eyes 2 of the user towards the object 56. When the user turns his/her head during the measurement, more distance values are measured by the distance sensor 54, which may indicate distances to different objects, such as the object 60 positioned in front of the head 52 of the user, in case the user directs his/her head in the direction of the object 60.

The wearable device 50 comprises a memory for storing the measured distance values. In the embodiment of FIG. 5, the wearable device 50 further comprises a control unit for further processing the measured distance values. However, it is also possible that the wearable device 50 merely measures and records the distance value and that further processing of the distance values is carried out at an external control unit. For example, this external control unit may be a general purpose computer or any other suitable control unit configured to receive the distance values. The external control unit may be located in a cloud, i.e., in one or more network servers accessible via a network connection. For example, the wearable device 50 may comprise an interface (e.g., a wired interface or a wireless interface) for outputting the measured distance values d(t). The (external) control unit may comprise an interface (e.g., a wired interface or a wireless interface) for inputting the measured distance values outputted via the interface of the wearable device 50.

In the embodiment of FIG. 5, the wearable device is a stand-alone device with an integrated control unit. However, as mentioned above, further embodiments are possible and also covered by the present disclosure, according to which the control unit is provided as an external device. The combination of the wearable device 50 and the control unit is also referred to as a system for determining a risk indicator for myopia.

The control unit receives the measured distance values and performs further processing of the distance values in order to determine a risk indicator for myopia.

More precisely, the control unit derives, from the measured time series of distance values d(t), at least a first distance value indicative of a distance between the wearable device (50) and an object located in a central vision area of the user (e.g., the object 56 shown in FIG. 5) and a second distance value indicative of a distance between the wearable device (50) and an object located in a peripheral vision area of the user (e.g., the object 60 shown in FIG. 5).

One way of distinguishing between first distance values and second distance values is to determine a temporal variability of the distance values d(t).

In this case, based on the measured time-dependent distance value d(t), the control unit determines a temporal variability of the distance value. The temporal variability may comprise or may correspond to at least one of a number of times the distance value changes from a value below a first predefined threshold value to a value above a second predefined threshold value within a predefined period, a number of times a time derivative of the distance value changes its sign within a predefined period, a difference between a maximum value of the distance value and a minimum value of the distance value within a predefined period, and a maximum of a time derivative of the distance value within a predefined period. The temporal variability is indicative of a degree of focal length changes and/or a frequency of focal length changes of the eyes 2 of the user.

Based on the temporal variability, the control unit determines whether a period of fixation exists. When the temporal variability of the measured distance values is below a first predefined threshold value during time intervals exceeding a second predefined threshold value, a period of fixation exists and distance values within this period are identified as first distance values. Distance values outside of periods of fixation are second distance values. These first and second distance values are then analyzed to determine a risk indicator for myopia. According to the present embodiment, the risk indicator is determined such that a higher mismatch between the first distance value and the second distance value leads to a risk indicator indicating a higher risk of myopia. In this case it can be assumed that a peripheral defocus situation occurs.

For example, as shown in FIG. 5, the user may turn his head 52 from the far object 56 to a nearby object 60 in order to look at the object 60. Hence, the lenses 16 of the eyes 2 of the user have to change their focal length to a shorter focal length in order to bring the object 60 into focus. In case the user turns his head 52 back to the object 56, the focal length has to be changed back to a longer focal length. In this case it is assumed that a period of fixation is a period in which the user directs his eyes 2 towards the central zone (along a central direction), i.e., to the object 56. Outside the periods of fixation, the eyes 2 of the user wander around in the peripheral zone, e.g., towards the object 60.

According to one or more embodiments, the wearable device 50 may comprise a movement sensor (e.g., an accelerometer and/or a gyroscope) for detecting a head movement of the user. Based on an output of the movement sensor, a direction is derived, into which the head 52 of the user is directed. Based on this direction and based on the measured distance values d(t), a first distance value (in the direction in which the head 52 of the user is turned) and a second (peripheral) distance value may be determined. The first distance value and the second distance value may then be processed by the control unit similar to the processing of the first distance value $d_c(t)$ and the second distance value $d_p(t)$ described below with regard to the second embodiment.

Figure 6:
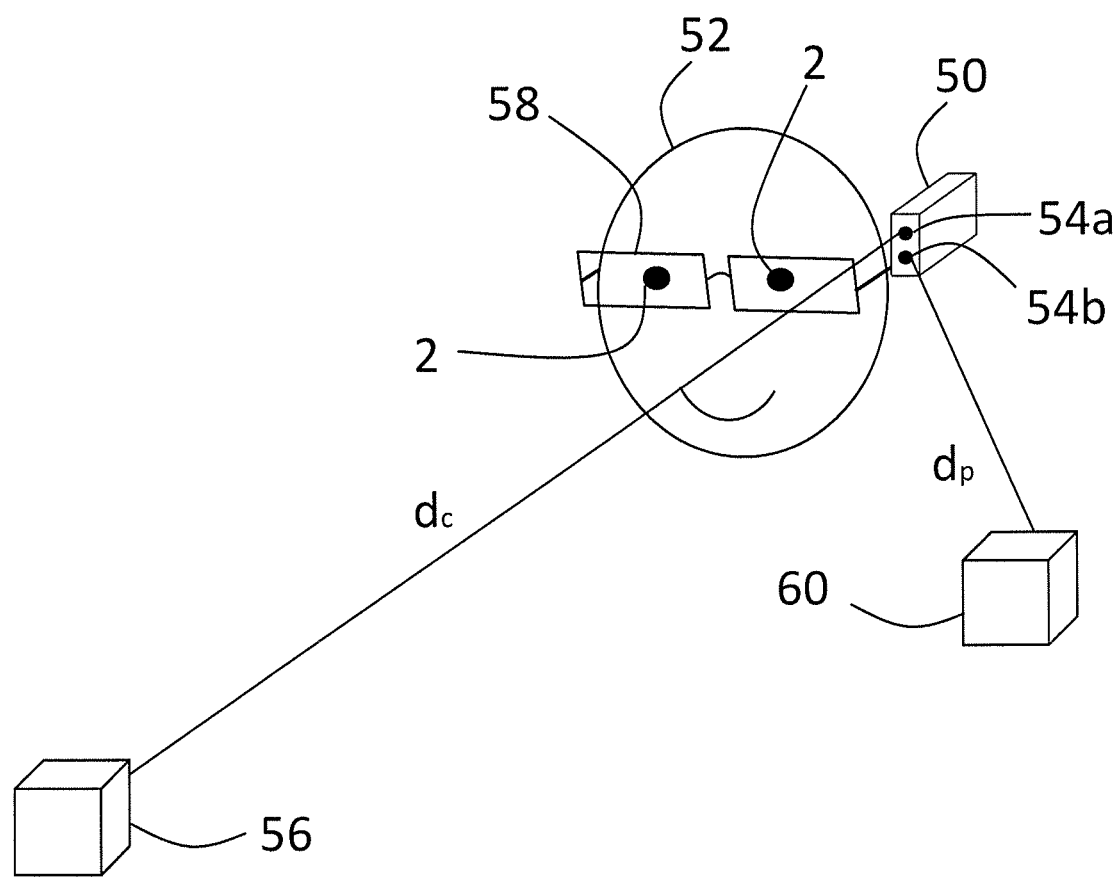
FIG. 6 shows a second embodiment of a wearable device with a plurality of distance sensors for determining a risk indicator for myopia.

FIG. 6 shows a wearable device 50 according to a second embodiment of the present disclosure. The wearable device 50 of the second embodiment is similar to the wearable device 50 of the first embodiment. Hence, the same reference signs are used in FIGS. 5 and 6 for indicating the same features. In the following, only the differences and additional features of the second embodiment will be explained, whereas the other features are the same as described above with regard to the first embodiment.

The wearable device 50 of the second embodiment comprises two distance sensors 54a and 54b. The first distance sensor 54a is directed along the central axis, similar to the distance sensor 54 of the first embodiment described above. The first distance sensor 54a time-dependently measures a first distance value $d_c(t)$ (central distance) indicating a distance between the wearable device 50 and an object 56 positioned along the central axis. The second distance sensor 54b time-dependently measures a second distance value $d_p(t)$ (peripheral distance) along a direction that is not identical to the central axis. In other words, the direction along which the second distance value $d_p(t)$ is measured, forms a predefined angle with regard to the first direction. In the embodiment of FIG. 6, the direction in which the second distance value $d_p(t)$ is measured (also referred to as a "peripheral direction") is turned to the side with regard to the central axis, such that both directions are substantially within a horizontal plane. According to other embodiments, the second distance value $d_p(t)$ could also be measured in a direction pointing downwards with regard to the central axis (i.e., with regard to the first direction $d_c$) or in a direction pointing both downwards and to the side with regard to the first direction $d_c$. In each case, the second, peripheral, direction is different to the first, central, direction. Hence, two different distance values, namely a first distance value $d_c(t)$ (central distance) relating to the first direction and a second distance value $d_p(t)$ (peripheral distance) relating to the second direction are measured and recorded (stored).

More precisely, the wearable device 50 performs a time-dependent measurement of the distance values $d_c(t)$ and $d_p(t)$. The control unit of the wearable device 50 receives and processes the first distance value $d_c(t)$ and the second distance value $d_p(t)$ and determines a risk indicator for myopia based on the first distance value $d_p(t)$ and on the second distance value $d_c(t)$.

The control unit of the wearable device 50 calculates a disparity (i.e., a mismatch) between the first distance value $d_c(t)$ and the second distance value $d_p(t)$ (more precisely, a time-dependent disparity value). The control unit determines an accumulated duration in which the difference (i.e., the time-dependent difference) is above a predefined threshold value within a predetermined period. The control unit further determines the risk indicator such that a higher accumulated duration leads to a risk indicator indicating a higher risk of myopia.

If the eye geometry (dimensions) is given it is possible to calculate directly the amount of induced peripheral defocus of the image of the object located at the distance $d_p(t)$, assuming that the eye is oriented towards and focused on the object located at the distance $d_c(t)$. This can be done by tracing the rays of light through the optical elements of the eye. If the eye geometry is not provided, calculation can assume the standard/default eye shape. The choice of default eye geometry can be based on the user demographics, like age, gender, ethnicity or other physiological/anatomical measures, such as prescription, height, eye length, corneal curvature, pupil size etc. In case the patient/user is using refractive correction, such as spectacles, contact lenses, etc. this optical elements can be also taken into account in calculation of peripheral hyperopic defocus.

In another implementation, a mathematical model can be derived, which links the time-dependent distances $d_p(t)$ and $d_c(t)$ to the hyperopic defocus. The approximate model of the amount of defocus can be derived based on machine learning methods with or without explicit calculations of the optical system of the eye.

In yet another implementation, a mathematical model can be derived for the myopia progression risk from time-dependent signals $d_c(t)$ and/or $d_p(t)$. The model might use explicit physical calculations of the peripheral defocus. The model might use the other signals collected with the wearable device, such as time-dependent ambient light intensity and spectral content, amount of movement, posture of the user, etc.

The model might use the information of the user's eye geometry/shape/dimensions. The model might use user's demographic and physiological/anatomical measures. The model might use genetical history of the eye diseases (history of myopia in the family). The model might include other known risk factors of myopia progression to improve prediction.

The model can be derived based on the historical/follow up data of myopia progression and the measurements of the time-dependent signals $d_c(t)$ and/or $d_p(t)$. For example, the model might be able to identify the statistics of $d_c(t)$ and/or $d_p(t)$ or derived defocus signals which typically lead to the myopia progression.

The model can be derived based on theoretical understandings of the myopia mechanism, on the statistics of observational data collected by other means, on the statistics of observational data collected by the (disclosed) wearable device or any combination.

A higher accumulated duration means that there are longer time periods within the predetermined period, in which the difference between the first distance value $d_c(t)$ and the second distance value $d_p(t)$ is larger than the predefined threshold value. In these time periods, it is likely that the user looks at an object at a greater distance (such as the object 56 shown in FIG. 6) while, at the same time, a different object having a shorter distance with respect to the eyes of the user (such as the object 60 shown in FIG. 6) causes a peripheral defocus as explained above. As further explained above, these situations may be a factor influencing the appearance of myopia. Hence, the risk indicator is higher in case such situations occur more often and/or over a longer period.

Under normal conditions in an awake state, the human body and head are in a state of permanent movement. Not all the movements are associated with the visual activities, for example, during walking the head movements are not necessary serving the purpose of aligning the gaze with the object. In order to be able to more correctly investigate focus shifts the processing may be necessary, which would involve interpretation of the origin and a purpose of head movements. This processing can be based on the distance signals $d_c(t)$ and $d_p(t)$ and can also be based on or combined with signals from other sensors, such as motion sensors (like accelerometer, gyroscope, magnetometer, etc.), position sensors (like geopositioning GPS, GLONASS, etc.) and other context sensors. Such context sensors can be a part of the wearable device.

For example, walking has a well-defined acceleration pattern, which can be recognized by accelerometers/gyroscopes and consequently compensated in CO and $d_p(t)$ signals to estimate the actual focus shifts.

Alternatively, during attention and vision demanding tasks humans are trying to suppress the unnecessary movements of the body and head. Thus the periods of attention/focusing can be identified from the statistics of $d_c(t)$ and $d_p(t)$, like for example reduced variations of distances in the specific time interval. The periods of focusing can be also identified from additional sensors (such as motion, rotation, position, etc.). For example, the accelerometer sensor can be used to detect the periods of focus as the periods of reduced motion/acceleration.

The present disclosure is not limited to the above embodiments. Instead of the one or two distance sensors, a camera or a three-dimensional distance scanner may be provided for time-dependently determining a first (central) distance value and a plurality of different second distance values pointing in different peripheral directions. Further, one or more sensors may be provided that simultaneously detect a plurality of distance sensors in different directions without scanning, by employing space-resolved sampling. Further, according to one or more embodiments, an eye tracking device is provided, which determines a viewing direction of the eyes of the user. In combination with a three-dimensional distance scanner, it can be decided, based on an output of the eye tracking device, which of the plurality of measured distance values is a central distance value with regard to the viewing direction and which distance values are peripheral distance values with regard to the viewing direction. The control unit may then use the central direction as first direction and one or more of the peripheral directions as second direction for the determination of the risk indicator. An advantage of using an eye tracking device may be that the results of the risk indicator are more accurate since the real viewing direction of the user may be considered.

As can be gathered from the above description of the embodiments, the wearable device 50 of the embodiments may allow measurements of peripheral defocus by sampling one or more distances around the user. The wearable device 50 may be intended to measure distance in a central zone (first distance value) and in a peripheral zone (second distance value). While it might be relatively simple to equip the user with an eye tracker (eye tracking device) and map the distances from a three-dimensional measurement equipment (such as camera or 3D-scanner) to the viewing direction from the eye tracker, as described above, it might be easier and cheaper to provide one or more distance sensors pointing in fixed directions, such as shown in the embodiments of FIGS. 5 and 6.

Hence, one approach relies on the fixed directions of the sensors in relation to the wearable device and, therefore, in relation to the head of the user. It is known that for the prolonged periods of visual activity or for challenging visual tasks, people tend to align the head with the direction of the gaze. The approach thus relies on such alignment and may use algorithms to be able to identify periods of alignments as well as periods of misalignments.

This may be done by analyzing signals from multiple sensors, for example, from inertial sensors provided in the wearable device. The distance in the central vision zone (first distance value) is measured with the centrally directed sensor (first distance sensor), while the peripheral zones can be probed with one or more sensors directed sideways (second distance value). In another implementation the peripheral zones may be sampled with the same sensor, by utilizing natural head movement of the user.

The wearable device 50 of one or more embodiments measure disparity of the near and far distances experienced by the user (wearer) at the different directions (part of retina).

Processing may include estimating the optical power in the central zone and optical power on the periphery and then determining the difference. The wearable device may 50 characterizes variability of the distances in the environment of the user.

Figure 7:
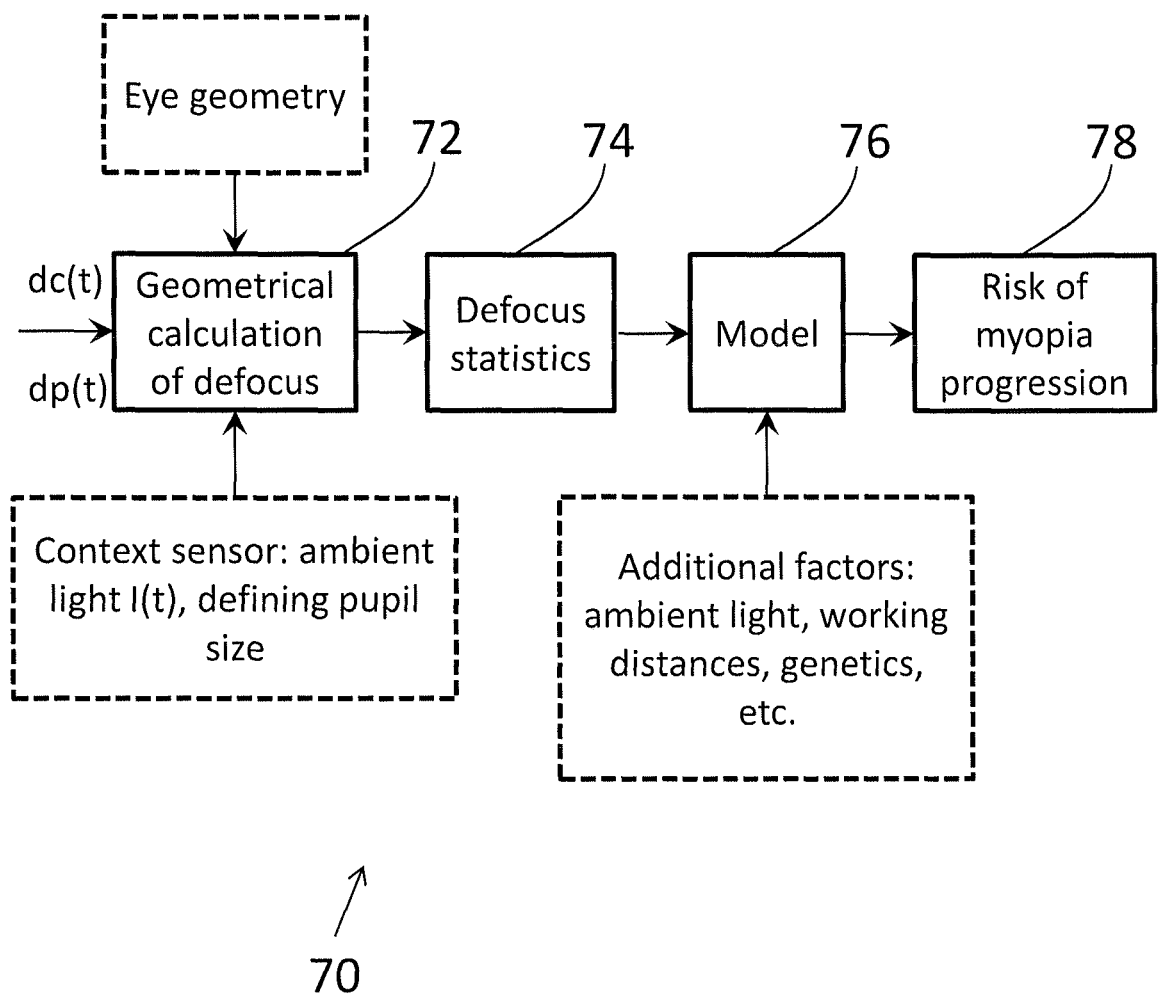
FIG. 7 shows a logical structure of a control unit of an embodiment of the present disclosure.

FIG. 7 shows the logical structure of a control unit 70 according to an embodiment of the present disclosure. For example, the control unit 70 may be provided as part of the wearable device 50 of the embodiment of FIG. 5 or FIG. 6.

FIG. 7 shows a plurality of components 72, 74, 76, 78. Each of these components may be provided in form of hardware or software.

A first component 72 is configured to perform geometrical calculation of defocus. Input parameters for the first component 72 are the time-dependent first distance value $t_c(t)$ and the time-dependent second distance value $t_p(t)$. Optional input parameters for the first component 72 are parameters defining the eye geometry (such as a shape of the eye 2) and parameters output by a context sensor of the wearable device 50. These parameters may relate to ambient light $1(t)$ measured by an ambient light sensor of the wearable device 50. Based on the aforementioned input parameters, the first unit 72 determines a time-dependent defocus.

The time-dependent defocus is output to a second component 74 which performs defocus statistics. In other words, the second component 74 observes the time-dependent defocus and statistically analyzes the defocus. Output parameters of the second component 74 are indicative of the defocus statistics.

A third component 76 is provided, which receives the defocus statistics and applies a model to the defocus statistics. Optional input parameters for the third component 73 are additional factors, such as ambient light, working distances, genetics, etc. These factors may have an influence concerning the risk of myopia. For example, a genetic factor may indicate that a particular user has an increased risk of myopia. This might lead to a higher risk indicator.

In a fourth component 78, the risk indicator is determined based on the output of the third component 76. As shown in FIG. 7, the risk indicator is determined on the basis of the first distance value $t_c(t)$ and the second distance value $d_p(t)$. Further, the optional parameters discussed above may have an influence on the determination of the risk indicator, such as the eye geometry, the output parameters of the context sensor, and/or the additional factors. Details regarding the determination of the risk indicator are described above with regard to the other embodiments.

In the following, examples and details of the model employed in the control unit are described with reference to FIGS. 8 to 13.

Figure 8:
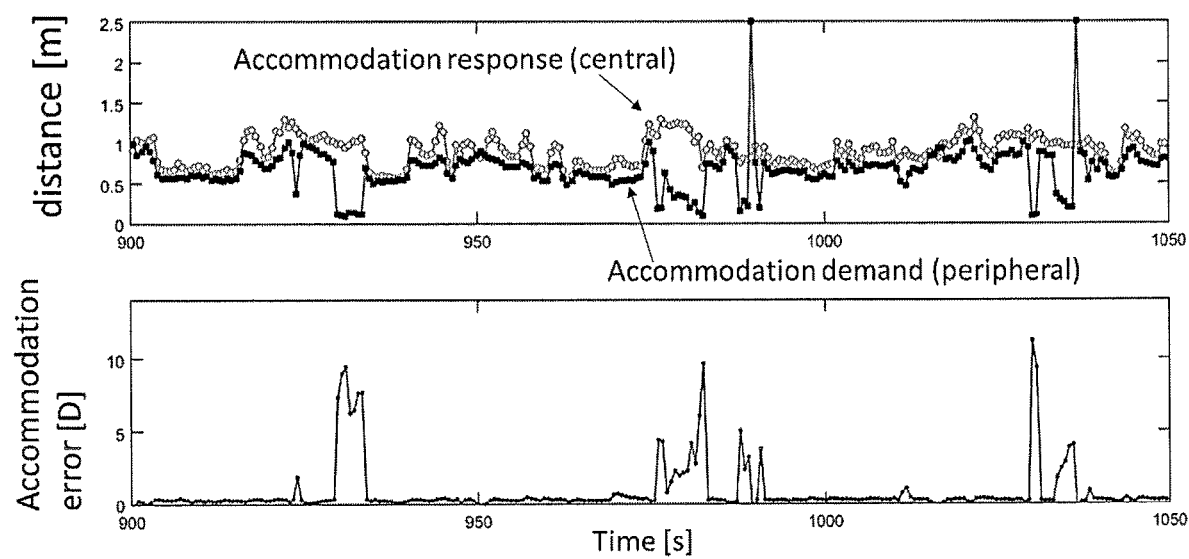
FIG. 8 shows an example of measurement results of the two distance sensors shown in FIG. 6 and a corresponding calculated mismatch.

FIG. 8 illustrates accommodation mismatch monitoring with double distance sensor system as described with regard to the embodiment of FIG. 6. The first distance sensor 54a is directed forward and aligned with central vision, the second distance sensor 54b is directed 30 degrees downwards and monitors demand of peripheral vision. In other words, the first distance value $d_c(t)$ is also referred to as "accommodation response" and the second distance value $d_p(t)$ is also referred to as "accommodation demand". The example of FIG. 8 shows an episode of desktop computer work with a distance to monitor around 0.8-1.0 meter. The second distance sensor 54b typically measures distance to the same monitor, which results in baseline accommodation error of 0.2-0.3 D, however, it also detects distances to the objects in the hands of the user, or desk, which results in errors reaching up to 10 diopters, which are integrated to produce estimate of myopia progression risk. It should be noted that in the present example, the accommodation error (or mismatch between first distance value and second distance value) is indicated in diopters (1/m).

Figure 9:
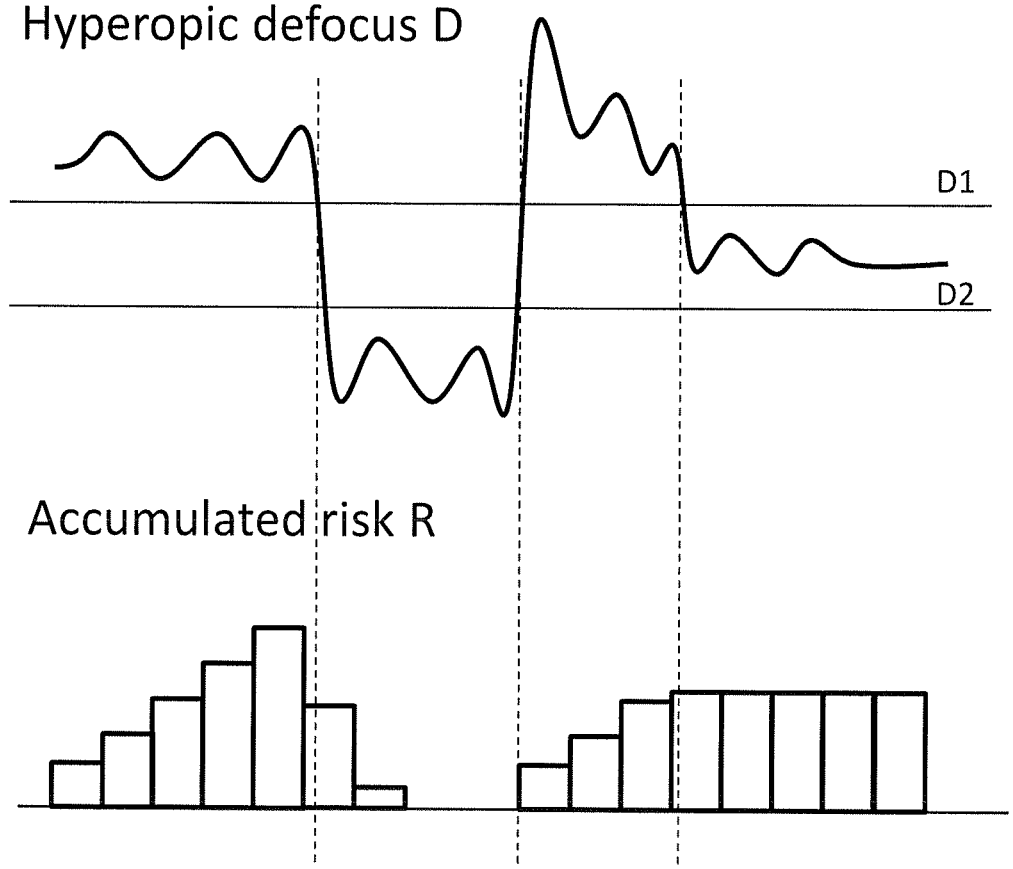
FIG. 9 shows a concept of a risk integrator that may be employed by the control unit.

FIG. 9 describes the concept of a risk integrator that may be employed by any of the control units described herein (in particular, by a control unit of the devices shown in FIG. 5 and/or FIG. 6). According to FIG. 9, the model of cumulative effect of myopia risk includes a reset mechanism. It has been shown in animal studies that a short period of absence of hyperopic accommodation error (clear vision) can neutralize accumulated effect of hyperopic defocus. This effect can be taken into account by introduction of integration window, for example in the form of leaky integrator which is slowly charging with hyperopic defocus and relatively faster discharging in the absence of hyperopic defocus.

In one implementation, a risk score can be a non-negative integer valued accumulator variable R which is incremented by a first value (e.g. 1) after each complete minute of sustained hyperopic defocus (D) above a first defined threshold (D1). At the same time, each minute of hyperopic defocus below a second defined threshold D2 (lower than the first threshold D1>D2) results in decrement of accumulator variable R by second value, which is expected to be larger by absolute value than the first value (e.g. 5). This assumes that defocus is signed with the positive value corresponding to hyperopic defocus and negative—to myopic.

Since R is non-negative, decrementing can only bring it to the minimal value of zero, so sustained period of clear vision or myopic defocus only keep the accumulator R at minimum, which implies absence of preventive effect of clear vision or myopic defocus.

In another implementation of risk integrator variable is R is real valued and non-negative and adjusted at each time step i according to following rule:

$$R(i)=f(D(i))+R(i-1), \text{ where } R>0$$

R(i) is a risk accumulator variable at time step i, R(i−1) is a same variable at previous time step, D(i) is real-valued hyperopic defocus and f(D) is a response function.

Figure 10:
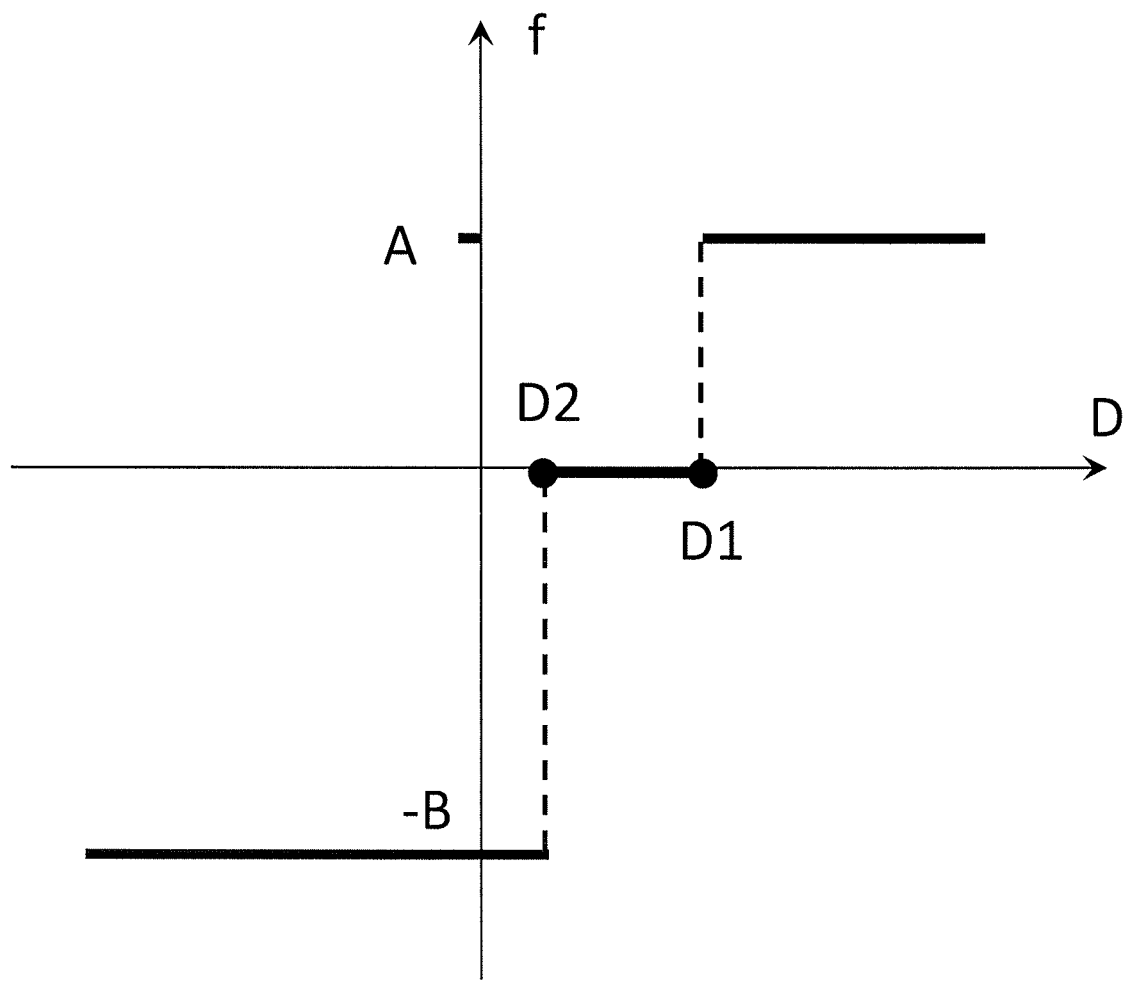
FIGS. 10 to 13 show different examples of response functions that may be used by the control unit for determining the risk indicator.

Response function can have a shape of step function as shown in FIG. 10:

$f(D)=A$ for $D>D1$ (hyperopic defocus charging) and $f(D)=-B$ for $D<D2$ (clear vision and myopic defocus discharging), $f(D)=0$ for $D2 \leq D \leq D1$ (indeterminacy/insensibility zone), where $D2<D1$ are predefined threshold values and $A,B>0$ (predefined values).

Figure 11:
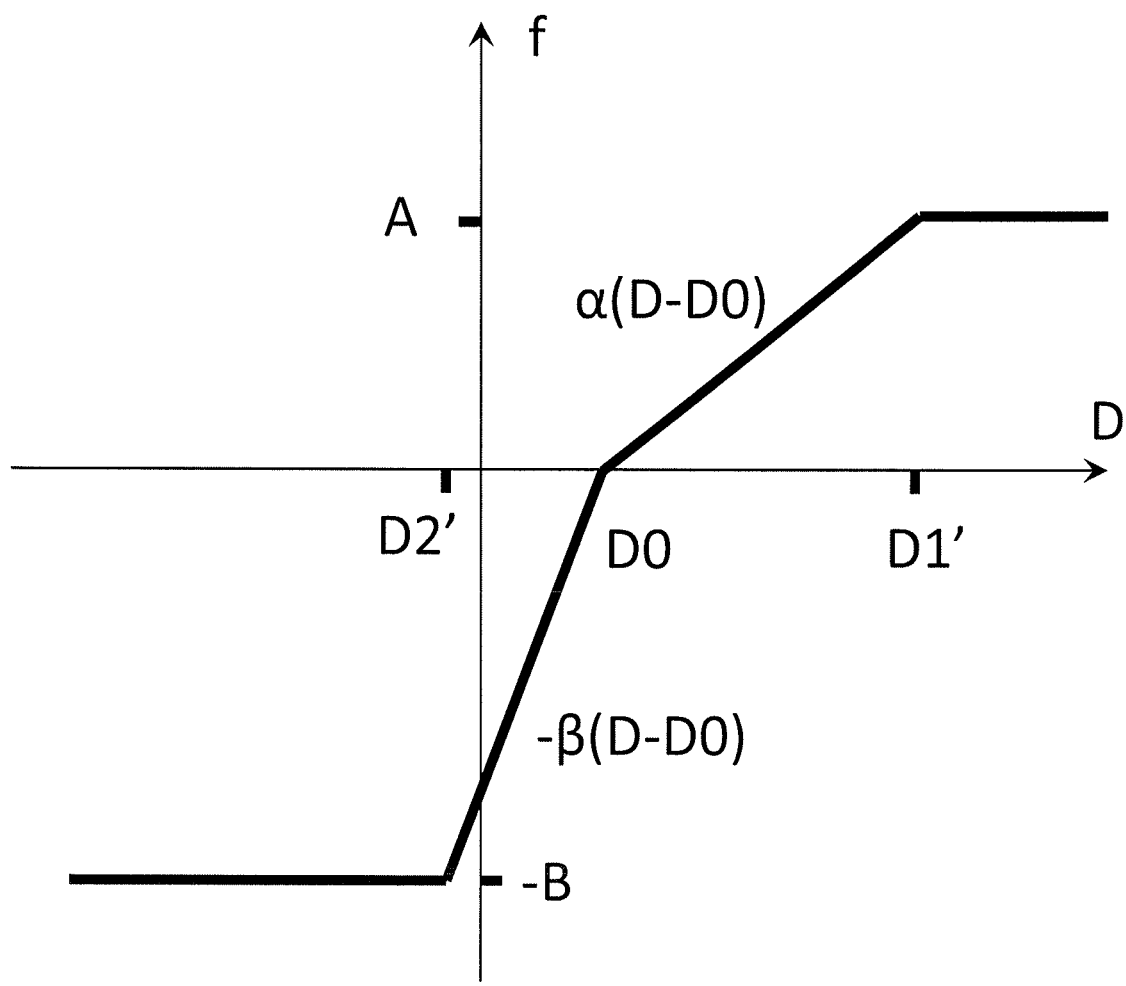

The response function can be more elaborated to include a linear dependence and saturation as shown in FIG. 11:

$f(D)=A$ for $D1'<D$ (saturation of hyperopic defocus charging)

$f(D)=\alpha(D-D0)$ for $D0<D<D1'$ (linear hyperopic defocus charging)

$f(x)=-\beta(D-D0)$ for $D2'<D<D0$ (linear clear vision/myopic defocus discharging), $f(x)=-B$ for $D<D2'$ (saturation clear vision/myopic defocus discharging), where $D2'<D0<D1'$ are threshold values and $\alpha, \beta, A, B>0$ and $A=\alpha(D1'-D0)$ and $B=-\beta(D2'-D0)$.

Figure 12:
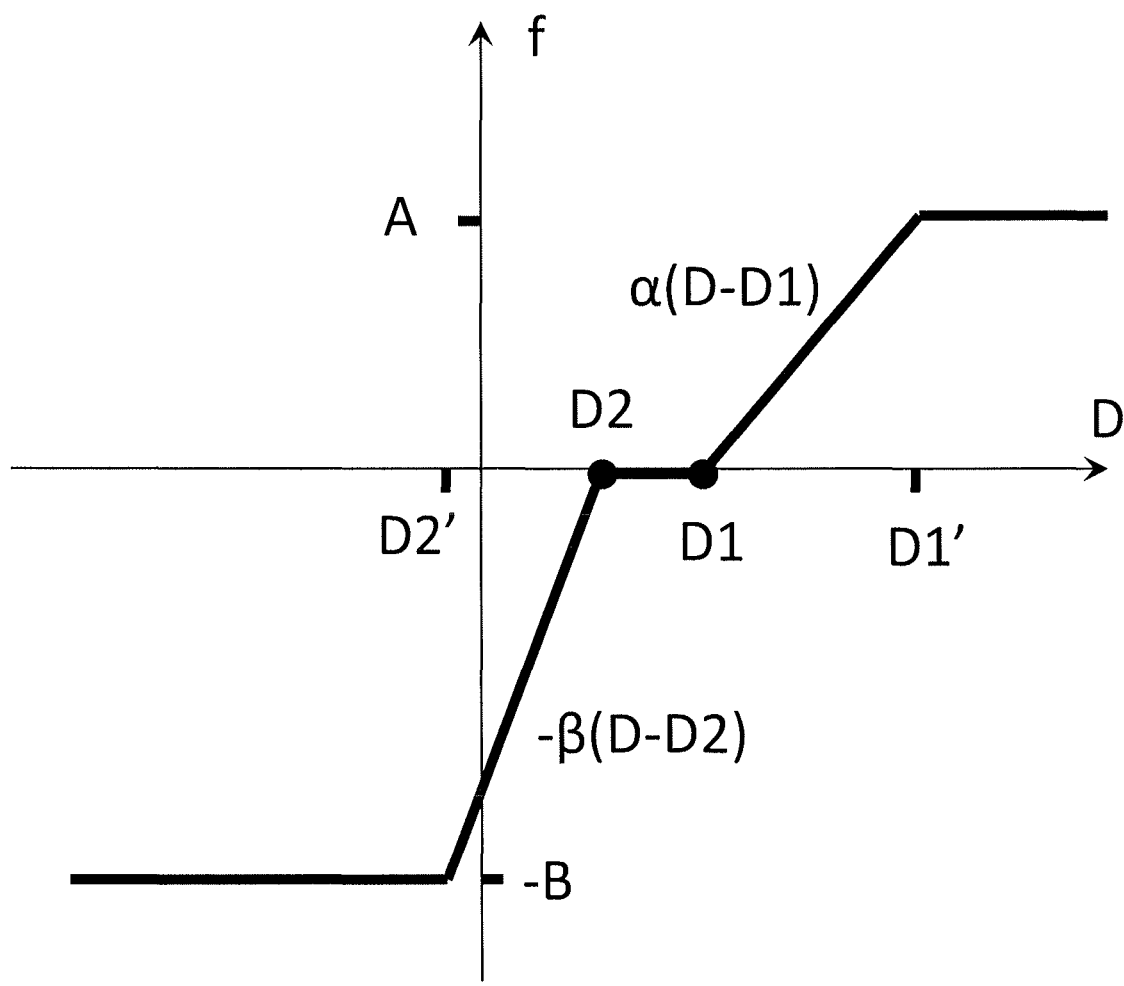
Figure 13:
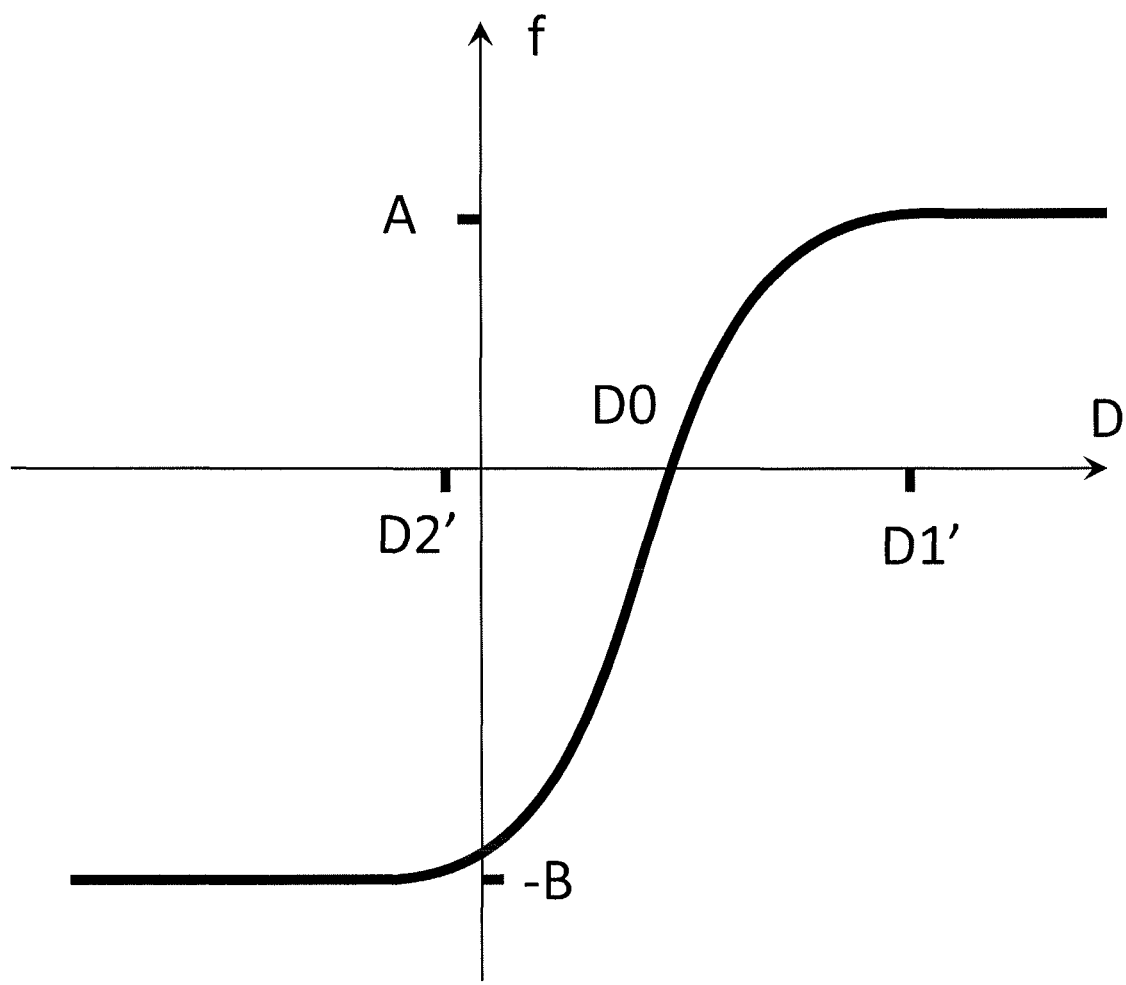

The response function can include linear dependence, saturation and insensibility zone as shown in FIG. 12:

$f(D)=A$ for $D1'<D$ (saturation of hyperopic defocus charging)

$f(D)=\alpha(D-D1)$ for $D1<D<D1'$ (linear hyperopic defocus charging)

$f(D)=0$ for $D1 \leq D \leq D2$ (indeterminacy/insensibility zone), $f(x)=-\beta(D-D2)$ for $D2'<D<D2$ (linear clear vision/myopic defocus discharging), $f(x)=-B$ for $D<D2'$ (saturation clear vision/myopic defocus discharging), where $D2'<D2<D1<D1'$ are threshold values and $\alpha, \beta, A, B > 0$ and $A=\alpha(D1'-D1)$ and $B=-\beta(D2'-D2)$.

The response function can have a form of sigmoid/logistic function, hyperbolic tangent, rectified linear unit, etc. or any combination. One example of a sigmoid function is shown, e.g., in FIG. 13.

In the above description and in the figures, the same reference numerals are used for corresponding features or units of different embodiments. However, the details expounded with regard to one of these features or units also hold accordingly for the features of other embodiments having the same reference sign. Further, the present invention is not limited to the embodiments described above, which are merely examples how the present invention could be carried out. The technique of the above disclosure and, in particular, the components of the control unit 70 may also be embodied in the form of a computer program product.

The invention claimed is:

1. A system for determining a risk indicator for myopia, the system comprising:
a wearable device configured to be attached to a body of a user, the wearable device comprising at least one distance sensor configured to determine at least a first distance value indicative of a distance between the wearable device and an object located in a central vision zone of the user and a second distance value indicative of a distance between the wearable device and an object located in a peripheral vision zone of the user;
a control unit configured to determine, based on the first distance value and the second distance value, a risk indicator for myopia.

2. The system of claim 1, wherein the control unit is configured to determine the risk indicator such that a higher mismatch between the first distance value and the second distance value leads to a risk indicator indicating a higher risk of myopia.

3. The system of claim 1, wherein the wearable device comprises a first distance sensor directed in a central direction towards the central vision zone of the user, wherein the first distance sensor is configured to determine the first distance value, and a second distance sensor directed in a peripheral direction towards the peripheral vision zone of the user, wherein the second distance sensor is configured to determine the second distance value.

4. The system of claim 1, wherein the distance sensor comprises a camera having a field of view including the central vision zone and the peripheral vision zone, wherein the distance sensor is configured to determine the first distance value and the second distance value based on one or more images captured by the camera.

5. The system of claim 1, wherein the control unit is configured to identify the first distance value during a period of fixation, when a variability of distance measurements of the distance sensor is below a first predefined threshold during time intervals exceeding a second predefined threshold and the second distance value is identified outside of the period of fixation.

6. The system of claim 1, wherein the wearable device comprises a motion sensor, and wherein the control unit is configured to identify periods of fixation as periods with a motion below a first predefined threshold during time intervals exceeding a second predefined threshold and to identify the first distance value during one of the periods of fixation and to identify the second distance value outside of the periods of fixation.

7. The system of claim 1, wherein the wearable device includes exactly one distance sensor for determining exactly one distance value at a given time, such that the exactly one distance sensor is configured to determine the first distance value and the second distance value at different times.

8. The system of claim 2, wherein the control unit is configured to determine an accumulated duration in which the mismatch between the first distance value and the second distance value is above a predefined threshold value within a predetermined period, and to determine the risk indicator such that a higher accumulated duration leads to a risk indicator indicating a higher risk of myopia.

9. The system of claim 1, wherein the wearable device comprises at least one additional sensor configured to output additional sensor data,
wherein the control unit is configured to determine, based on the additional sensor data and based on an output of the at least one distance sensor, the first distance value and the second distance value, and, optionally,
wherein the additional sensor comprises at least one of an orientation sensor for determining an orientation of the wearable device, a position sensor device for determining a position of the wearable device and an acceleration sensor for determining an acceleration of the wearable device.

10. The system of claim 1, wherein the wearable device comprises an eye tracking device for determining a viewing direction of an eye of the user and, optionally,
wherein the control unit is configured to determine, based on the determined viewing direction and based on an output of the at least one distance sensor, the first distance value for indicating a distance to an object located at an optical axis of the eye and the second distance value for indicating a distance to an object located at a peripheral direction forming a predefined angle larger than zero with respect to the optical axis of the eye.

11. The system of claim 1 wherein
the wearable device further comprises a light sensor for determining a light intensity and/or spectral content, and
the control unit is configured to determine the risk indicator based on the light intensity and/or spectral content.

12. The system of claim 1, wherein the control unit is further configured to determine the risk indicator based on a type of activity detected by the wearable device.

13. The system of claim 1, wherein the wearable device comprises the control unit.

14. A method for determining a risk indicator for myopia, the method comprising:
determining at least a first distance value indicative of a distance between a wearable device attached to a body of a user and an object located in a central vision zone of the user and a second distance value indicative of a distance between the wearable device and an object located in a peripheral vision zone of the user;

determining, based on the first distance value and the second distance value, a risk indicator for myopia.

15. A computer program stored on a non-transitory computer-readable storage medium, the computer program comprising instructions which, when the program is executed by a computer, cause the computer to:

determine at least a first distance value indicative of a distance between a wearable device attached to a body of a user and an object located in a central vision zone of the user and a second distance value indicative of a distance between the wearable device and an object located in a peripheral vision zone of the user;

determine, based on the first distance value and the second distance value, a risk indicator for myopia.

* * * * *